United States Patent
King et al.

(10) Patent No.: US 11,944,656 B2
(45) Date of Patent: Apr. 2, 2024

(54) MICROBIALS FOR FEED

(71) Applicants: MICROBIAL DISCOVERY GROUP, LLC, Franklin, WI (US); UNITED ANIMAL HEALTH, INC., Sheridan, IN (US)

(72) Inventors: Michael R. King, Oak Creek, WI (US); Sona Son, Cudahy, WI (US); Kyle Leistikow, Franklin, WI (US); Joel D. Spencer, Westfield, IN (US)

(73) Assignees: MICROBIAL DISCOVERY GROUP, LLC, Franklin, IN (US); UNITED ANIMAL HEALTH, INC., Sheridan, IN (US)

( * ) Notice: Subject to any disclaimer, the term of this patent is extended or adjusted under 35 U.S.C. 154(b) by 125 days.

(21) Appl. No.: 17/050,982

(22) PCT Filed: May 1, 2019

(86) PCT No.: PCT/US2019/030182
§ 371 (c)(1),
(2) Date: Oct. 27, 2020

(87) PCT Pub. No.: WO2019/213243
PCT Pub. Date: Nov. 7, 2019

(65) Prior Publication Data
US 2021/0236563 A1    Aug. 5, 2021

Related U.S. Application Data

(60) Provisional application No. 62/778,495, filed on Dec. 12, 2018, provisional application No. 62/665,380, filed on May 1, 2018.

(51) Int. Cl.
| | |
|---|---|
| A61K 35/742 | (2015.01) |
| A23K 10/18 | (2016.01) |
| A23K 20/189 | (2016.01) |
| A23K 20/195 | (2016.01) |
| A23K 50/30 | (2016.01) |
| A23L 33/135 | (2016.01) |
| A61K 38/46 | (2006.01) |
| A61P 19/04 | (2006.01) |

(52) U.S. Cl.
CPC ............ *A61K 35/742* (2013.01); *A23K 10/18* (2016.05); *A23K 20/189* (2016.05); *A23K 20/195* (2016.05); *A23K 50/30* (2016.05); *A23L 33/135* (2016.08); *A61K 38/465* (2013.01); *A61P 19/04* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 4,673,638 A | 6/1987 | Grosch et al. | |
| 2004/0220093 A1* | 11/2004 | Stern et al. | A61K 38/17 514/12 |
| 2010/0092428 A1 | 4/2010 | Schmidt et al. | |
| 2015/0216203 A1 | 8/2015 | Isaksen et al. | |
| 2017/0246224 A1 | 8/2017 | King et al. | |
| 2019/0021341 A1 | 1/2019 | Davis et al. | |

FOREIGN PATENT DOCUMENTS

WO    WO2018148847    8/2018

OTHER PUBLICATIONS

Hossain et al., "Probiotics as potential alternative biocontrol agents in the agriculture and food industries: A review", Food Research International, vol. 100, pp. 63-73 (Year: 2017).*
Hoar et al., "Production Cycle of Swine", U.S. Food and Drug Administration and Western Institute for Food Safety & Security, pp. 1-10 (Year: 2015).*
Woyengo et al., "Review: Supplementation of phytase and carbohydrases to diets for poultry", Canadian Journal of Animal Science, vol. 91, No. 2, pp. 177-192 (Year: 2011).*
Sanad et al., "Insights into potential pathogenesis mechanisms associated with Campylobacter jejuni-induced abortion in ewes", BMC Veterinary Research, vol. 10(274, pp. 1-13 (Year: 2014).*
PCT Search Report and Written Opinion prepared for PCT/US2019/030182, completed Aug. 13, 2019.
Zganjer, Mirko, et al., "Treatment of Rectal Prolapse in Children with Cow Milk Injection Sclerotherapy: 30-Year Experience," Feb. 7, 2008, World Journal of Gastroenterology, vol. 14, No. 5, pp. 747-740.

* cited by examiner

*Primary Examiner* — Michelle F. Paguio Frising
*Assistant Examiner* — Grant C Currens
(74) *Attorney, Agent, or Firm* — Barnes & Thornburg, LLP

(57) ABSTRACT

The invention relates to direct-fed microbials for use in *E. coli*, *Salmonella*, and/or *Campylobacter* inhibition in animals. More particularly, the invention relates to isolated *Bacillus* strains A12, 54, 681, 101, 235, and 721, and strains having all of the identifying characteristics of these strains, for a use comprising the above-mentioned use. The invention also relates to the use of isolated *Bacillus* strains 681, 721, A12, 54, 86, 300, 101, 102, 235, and 177, and strains having all of the identifying characteristics of these strains, to prevent or reduce prolapse in an animal.

17 Claims, 14 Drawing Sheets

| Salmonella | 681 | 721 |
|---|---|---|
| Isolate S1 | + | + |
| Isolate S2 | + | +/- |
| Isolate S3 | + | + |
| Isolate S4 | + | + |
| Isolate S5 | + | + |
| Isolate S6 | + | + |
| Isolate S7 | + | + |
| Isolate S8 | + | + |
| Isolate S9 | + | + |
| Isolate S10 | + | + |
| Isolate S11 | + | + |
| Isolate S12 | + | +/- |
| Isolate S13 | + | +/- |
| Isolate S14 | + | + |
| Isolate S15 | + | + |
| Isolate S16 | + | + |
| Isolate S17 | + | + |
| Isolate S18 | + | + |
| Isolate S19 | + | + |
| Isolate S20 | + | + |
| Isolate S21 | + | + |
| Isolate S22 | + | + |
| Isolate S23 | + | + |
| Isolate S24 | + | + |
| Isolate S25 | + | + |
| Isolate S26 | + | + |
| Isolate S27 | + | + |
| Isolate S28 | + | + |
| Isolate S29 | + | + |
| Isolate S30 | + | + |
| Isolate S31 | + | + |
| Isolate S32 | + | + |
| Isolate S33 | + | + |
| Isolate S34 | + | + |
| Isolate S35 | + | + |
| Isolate S36 | + | + |

FIGURE 1A

| Campylobacter | 681 | 721 |
|---|---|---|
| Isolate Ca1 | + | + |
| Isolate Ca2 | + | + |
| Isolate Ca3 | + | + |
| Isolate Ca4 | + | + |
| Isolate Ca5 | + | + |
| Isolate Ca6 | + | + |
| Isolate Ca7 | + | + |
| Isolate Ca8 | + | + |
| Isolate Ca9 | + | + |
| Isolate Ca10 | + | + |
| Isolate Ca11 | + | + |
| Isolate Ca12 | + | + |
| Isolate Ca13 | + | + |
| Isolate Ca14 | + | + |
| Isolate Ca15 | + | + |

FIGURE 1B

| E. coli | 681 |
|---|---|
| Isolate Ec1 | + |
| Isolate Ec2 | + |
| Isolate Ec3 | + |
| Isolate Ec4 | + |
| Isolate Ec5 | +/- |
| Isolate Ec6 | + |
| Isolate Ec7 | +/- |
| Isolate Ec8 | + |
| Isolate Ec9 | + |
| Isolate Ec10 | + |
| Isolate Ec11 | +/- |
| Isolate Ec12 | +/- |
| Isolate Ec13 | + |
| Isolate Ec14 | +/- |
| Isolate Ec15 | + |
| Isolate Ec16 | + |
| Isolate Ec17 | +/- |
| Isolate Ec18 | +/- |
| Isolate Ec19 | + |
| Isolate Ec20 | + |
| Isolate Ec21 | +/- |
| Isolate Ec22 | +/- |
| Isolate Ec23 | +/- |
| Isolate Ec24 | + |
| Isolate Ec25 | +/- |
| Isolate Ec26 | +/- |
| Isolate Ec27 | +/- |
| Isolate Ec28 | + |
| Isolate Ec29 | + |
| Isolate Ec30 | +/- |
| Isolate Ec31 | +/- |
| Isolate Ec32 | + |
| Isolate Ec33 | + |
| Isolate Ec34 | + |
| Isolate Ec35 | +/- |
| Isolate Ec36 | + |

FIGURE 1C

| E. coli | A12 | 54 |
|---|---|---|
| B1 | + | +/- |
| B2 | + | +/- |
| C8 | + | + |
| C9 | + | +/- |
| B12 | + | +/- |
| 3.3 | + | + |
| E12 | + | + |
| A8 | +/- | +/- |
| D8 | - | +/- |
| D9 | - | +/- |
| B12 | +/- | +/- |
| 2.5 | + | +/- |
| B5 | - | +/- |
| A6 | + | +/- |
| A9 | - | +/- |
| B10 | + | +/- |
| A8 | + | +/- |
| C6 | + | + |
| F8 | +/- | +/- |
| F5 | + | +/- |
| F10 | +/- | +/- |
| F7 | + | +/- |
| H10 | - | +/- |
| H7 | + | +/- |
| F2 | + | +/- |
| H1 | +/- | +/- |
| G10 | + | +/- |
| G8 | + | +/- |
| C6 | + | +/- |
| D8 | + | + |
| E3 | +/- | +/- |
| E4 | +/- | +/- |
| E10 | +/- | - |
| C4 | + | +/- |
| D3 | + | +/- |
| C10 | + | +/- |
| F4 | + | +/- |
| A4 | +/- | +/- |
| B11 | + | - |
| B12 | + | +/- |
| C4 | + | - |
| H3 | + | + |
| H5 | + | + |
| G5 | + | + |
| G6 | + | - |
| H6 | + | + |
| G7 | +/- | + |
| E8 | +/- | + |
| G8 | + | +/- |
| F4 | + | +/- |
| F6 | + | - |
| F10 | + | - |
| G7 | + | - |

FIGURE 2A

|      | A12 | 54  |
|------|-----|-----|
| A5   | +   | +   |
| A6   | +   | +   |
| A9   | +   | +   |
| A11  | +   | +   |
| C8   | +   | +   |
| D1   | +   | +   |
| B7   | +   | +/- |
| D1   | +   | +   |
| A2   | +   | +   |
| B12  | +/- | +   |
| A3   | +   | +/- |
| B7   | +   | +/- |
| E12  | +   | +/- |
| E4   | +/- | +/- |
| E6   | +/- | +/- |
| E3   | +   | +/- |
| G3   | +   | +/- |
| G7   | +   | +/- |
| E9   | +   | +/- |
| A1   | +   | +/- |
| B1   | +   | +/- |
| C1   | +   | +/- |
| A11  | +   | +/- |
| B10  | +   | +/- |
| B12  | +   | +/- |
| C12  | +   | +/- |
| G5   | +   | +/- |
| H5   | +   | +/- |
| F6   | +   | +   |
| G6   | +   | +   |
| F7   | +   | +/- |
| E8   | +   | +/- |
| F8   | +   | +/- |
| E9   | +   | +/- |
| H9   | +   | +/- |
| E2   | +   | +/- |
| E3   | +   | +/- |
| G4   | +   | +/- |
| G7   | +   | +/- |
| B8   | +   | +/- |
| E8   | +   | +/- |
| B9   | +   | +/- |
| F12  | +   | +/- |
| B1   | +   | +/- |
| B2   | +   | +/- |
| B8   | +   | +/- |
| C10  | +   | +/- |

FIGURE 2B

| Salmonella | A12 | 54  |
|------------|-----|-----|
| WV-1       | +/- | +/- |
| WV-2       | +/- | +/- |
| WV-3       | +/- | +/- |

FIGURE 2C

MDG *Bacillus* isolates

| | 86 | 101 | 102 | 177 | 235 | 300 | A12 | 681 | 721 | B4 |
|---|---|---|---|---|---|---|---|---|---|---|
| B9 | | | 0 | | | 2 | 11 | 0 | 0 | |
| D9 | | | 0 | | | 0 | 13 | 0 | 0 | |
| A10 | | | 0 | | | 0 | 11 | 0 | 0 | |
| G12 | | | 5 | | | 7 | 12 | 9 | 8 | |
| H12 | | | 5 | | | 7 | 12 | 9 | 7 | |
| A1 | 9 | 9 | 1 | 1 | 5 | 5 | 9 | 4 | 5 | 6 |
| B1 | 9 | 8 | 2 | 1 | 5 | 5 | 9 | 4 | 6 | 6 |
| C1 | 9 | 8 | 1 | 1 | 10 | 10 | 10 | 4 | 6 | 5 |
| D1 | 9 | 7 | 2 | 1 | 6 | 5 | 10 | 5 | 5 | 6 |
| E1 | 10 | 10 | 5 | 1 | 10 | 6 | 10 | 5 | 15 | 10 |
| F1 | 10 | 10 | 6 | 1 | 5 | 6 | 10 | 5 | 8 | 10 |
| G1 | 20 | 10 | 2 | 1 | 4 | 6 | 9 | 5 | 7 | 7 |
| H1 | 8 | 7 | 1 | 1 | 5 | 1 | 9 | 4 | 2 | 2 |
| A2 | 9 | 7 | 2 | 1 | 4 | 3 | 9 | 4 | 5 | 5 |
| B2 | 9 | 6 | 2 | 1 | 4 | 5 | 9 | 4 | 5 | 5 |
| C2 | 9 | 7 | 3 | 1 | 6 | 5 | 10 | 5 | 7 | 9 |
| D2 | 8 | 6 | 2 | 1 | 6 | 6 | 10 | 5 | 6 | 9 |
| E2 | 8 | 5 | 2 | 1 | 5 | 6 | 11 | 5 | 5 | 7 |
| F2 | 8 | 5 | 2 | 1 | 5 | 6 | 10 | 4 | 5 | 7 |
| G2 | 8 | 5 | 2 | 1 | 5 | 6 | 10 | 4 | 5 | 7 |
| H2 | 9 | 5 | 2 | 1 | 5 | 5 | 10 | 4 | 4 | 6 |
| A3 | 7 | 8 | 1 | 1 | 5 | 7 | 10 | 2 | 5 | 9 |
| B3 | 7 | 8 | 1 | 1 | 3 | 7 | 10 | 2 | 5 | 7 |
| C3 | 7 | 8 | 2 | 2 | 4 | 8 | 10 | 2 | 5 | 7 |
| D3 | 7 | 9 | 2 | 1 | 4 | 8 | 11 | 2 | 5 | 7 |

*Campylobacter* isolates

FIGURE 5

MICROBIALS FOR FEED

CROSS-REFERENCE TO RELATED APPLICATIONS

This application is a national stage entry under 35 U.S.C. § 371 of PCT International Application Number PCT/US2019/030182, filed May 1, 2019, which claims the benefit of and priority to U.S. Provisional Patent Application No. 62/778,495, filed Dec. 12, 2018 and U.S. Provisional Patent Application No. 62/665,380, filed May 1, 2018, the entire disclosures of which are incorporated herein by reference.

FIELD OF THE DISCLOSURE

The invention relates to direct-fed microbials for use in *E. coli*, *Salmonella*, and *Campylobacter* inhibition in animals. More particularly, the invention relates to isolated *Bacillus* strains 681, 721, A12, 101, 235, and 54, and strains having all of the identifying characteristics of these strains, for a use comprising the above-mentioned use. The invention also relates to the use of isolated *Bacillus* strains 681, 721, A12, 54, 86, 300, 101, 102, 235, and 177, and strains having all of the identifying characteristics of these strains, to prevent or reduce or control prolapse in an animal.

BACKGROUND AND SUMMARY OF THE INVENTION

The present invention relates to direct-fed microbial (DFM) compositions and methods for *E. coli*, *Salmonella*, and *Campylobacter* inhibition in an animal. An animal's gastrointestinal tract is constantly challenged by large numbers of bacteria, viruses, fungi, and protozoa found in feed, bedding, and the environment. The gastrointestinal tract has a sophisticated system to counter these potential pathogens consisting of physical, chemical, and immunological lines of defense. Beneficial bacteria are an important part of this system because they provide animals with bacteria that assist in establishment (or reestablishment) of a normal bacterial profile, they strengthen the animal's immune system, and they help to fight disease (e.g., disease caused by *E. coli*, *Salmonella*, and *Campylobacter* in animals). Due to the importance of preventing and treating *E. coli*, *Salmonella*, and *Campylobacter* disease in animals, both to the agricultural industry, and to the human food supply, direct-fed microbial strains are needed that inhibit *E. coli*, *Salmonella*, and *Campylobacter* in animals, such as agricultural animals.

Applicants have developed direct-fed microbials that result in *E. coli*, *Salmonella*, and *Campylobacter* inhibition. The direct-fed microbials and compositions comprising the direct-fed microbials described herein offer a commercial benefit by providing *E. coli*, *Salmonella*, and *Campylobacter* inhibition in animals, such as agricultural animals. In addition, the direct-fed microbial compositions described herein result in a reduction or elimination in the use of antibiotics which reduces the overall cost of animal feed and reduces the development of antibiotic resistance.

Furthermore, there has been a general and widespread increase in the incidence of prolapse (e.g., rectal prolapse) in animals, such as agricultural animals. The factors affecting the incidence for prolapses include factors related to nutrition, physiology, hormones, genetics, and environment. Applicants have developed direct-fed microbials for reducing or preventing prolapse in animals, such as agricultural animals. The prolapses include vaginal and/or uterine prolapse and rectal and/or anal prolapse.

Methods and compositions are provided for inhibiting *E. coli*, *Salmonella*, and *Campylobacter* in animals. In various embodiments, the animal can be selected from the group consisting of a poultry species, a porcine species, a caprine species, a bovine species, an ovine species, an equine species, and a companion animal. In the embodiment where the animal is a poultry species, the poultry species can be selected from the group consisting of a broiler, a chicken, a layer, a breeder, a turkey, a turkey poult, a gosling, a duckling, a guineakeet, a pullet, a hen, a rooster, a cockerel, and a capon. In the embodiment where the animal is a porcine species, the porcine species can be selected from the group consisting of a grow finish pig, a nursery pig, a sow, and a breeding stock pig.

In various embodiments, the compositions for use in the methods described herein can be a commercial package, a feed additive for an animal feed composition, an additive for the drinking water of an animal, or an animal feed composition (e.g., a complete feed), each comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof.

In one embodiment of the methods described herein, a method is provided of feeding an animal. The method comprises the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, wherein the *Bacillus* strain causes *E. coli*, *Salmonella*, and/or *Campylobacter* inhibition in the animal.

In another embodiment of the methods described herein, a method is provided of controlling a detrimental effect of *E. coli*, *Salmonella*, and/or *Campylobacter*. The method comprises the steps of administering to an animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, and controlling the detrimental effect of *E. coli, Salmonella,* and/or *Campylobacter* in the animal.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain prevents or reduces prolapse in the animal.

In still another embodiment, a method of controlling a detrimental effect of *E. coli* and/or *Campylobacter* is provided. The method comprises the steps of administering to an animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, and controlling the detrimental effect of *E. coli* and/or *Campylobacter* in the animal wherein the detrimental effect is prolapse in the animal.

In another embodiment of the methods described herein, a method is provided of feeding an animal. The method comprises the step of administering to the animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, wherein the *Bacillus* strain causes *Campylobacter* inhibition in the animal.

In another embodiment of the methods described herein, a method is provided of controlling a detrimental effect of *Campylobacter*. The method comprises the steps of administering to an animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, and controlling the detrimental effect of *Campylobacter* in the animal.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the EXAMPLES are applicable to any of the following embodiments of the invention described in the numbered clauses below.

1. A method of feeding an animal, the method comprising the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, wherein the *Bacillus* strain causes *E. coli, Salmonella,* and/or *Campylobacter* inhibition in the animal.

2. The method of clause 1 wherein the animal is selected from the group consisting of a poultry species, a porcine species, a caprine species, a bovine species, an ovine species, an equine species, and a companion animal.

3. The method of clause 2 wherein the poultry species is a broiler chicken.

4. The method of any one of clauses 1 to 3 wherein the *E. coli, Salmonella,* and/or *Campylobacter* inhibition prevents *E. coli, Salmonella,* and/or *Campylobacter* disease in the animal.

5. The method of any one of clauses 1 to 3 wherein the *E. coli, Salmonella*, and/or *Campylobacter* inhibition reduces *E. coli, Salmonella*, and/or *Campylobacter* disease in the animal.
6. The method of clause 2 wherein the animal is a porcine species and the porcine species is selected from the group consisting of a grow finish pig, a nursery pig, a sow, and a breeding stock pig.
7. The method of any one of clauses 1 to 6 wherein the *Bacillus* strain produces an enzyme selected from the group consisting of an α-galactosidase, a protease, a lipase, an amylase, a xylanase, a cellulase, and combinations thereof.
8. The method of any one of clauses 1 to 7 further comprising the step of administering to the animal another bacterial strain selected from the group consisting of another *Bacillus* strain, a lactic acid bacterial strain, and combinations thereof.
9. The method of any one of clauses 1 to 8 wherein the strain administered is *Bacillus* strain A12 (NRRL No. B67516) or a strain having all of the identifying characteristics of *Bacillus* strain A12 (NRRL No. B67516).
10. The method of any one of clauses 1 to 8 wherein the strain administered is *Bacillus* strain 54 (NRRL No. B67517) or a strain having all of the identifying characteristics of *Bacillus* strain 54 (NRRL No. B67517).
11. The method of any one of clauses 1 to 8 wherein the strain administered is *Bacillus* strain 681 (NRRL No. B67515) or a strain having all of the identifying characteristics of *Bacillus* strain 681 (NRRL No. B67515).
12. The method of any one of clauses 1 to 8 wherein the strain administered is *Bacillus* strain 721 (NRRL No. B67514) or a strain having all of the identifying characteristics of *Bacillus* strain 721 (NRRL No. B67514).
13. The method of any one of clauses 1 to 12 wherein the *Bacillus* strain is administered in the feed composition at a dose of about $1.0 \times 10^3$ CFU/gram of the feed composition to about $5.0 \times 10^{12}$ CFU/gram of the feed composition.
14. The method of any one of clauses 1 to 12 wherein the *Bacillus* strain is administered in the feed composition at a dose of about $1.0 \times 10^3$ CFU/gram of the feed composition to about $1.0 \times 10^7$ CFU/gram of the feed composition.
15. The method of any one of clauses 1 to 14 wherein the *Bacillus* strain is administered in the feed composition at a dose greater than about $7.0 \times 10^4$ CFU/gram of the feed composition.
16. The method of any one of clauses 1 to 15 wherein the *Bacillus* strain is administered in the feed composition at a dose of about $7.3 \times 10^4$ CFU/gram of the feed composition.
17. The method of any one of clauses 1 to 16 wherein the *Bacillus* strain is isolated from a high performing grow finish pig.
18. The method of any one of clauses 1 to 17 further comprising the step of administering an antibiotic to the animal.
19. The method of any one of clauses 1 to 18 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
20. The method of clause 19 wherein the enzyme is an NSPase or a phytase.
21. The method of any one of clauses 1 to 20 wherein the microbial balance in the animal is maintained.
22. The method of clause 2 wherein the animal is a companion animal.
23. The method of clause 22 wherein the animal is a canine species or a feline species.
24. The method of clause 2 wherein the animal is a sow and the *Bacillus* strain is administered during lactation.
25. The method of clause 2 wherein the animal is a sow and the *Bacillus* strain is administered during gestation.
26. The method of any one of clauses 1 to 25 wherein the feed composition is administered daily to the animal.
27. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.
28. A method of controlling a detrimental effect of *E. coli, Salmonella*, and/or *Campylobacter*, the method comprising the steps of administering to an animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, and controlling the detrimental effect of *E. coli, Salmonella*, and/or *Campylobacter* in the animal.
29. The method of clause 28 wherein the animal is selected from the group consisting of a poultry species, a porcine species, a caprine species, a bovine species, an ovine species, an equine species, and a companion animal.
30. The method of clause 29 wherein the poultry species is a broiler chicken.
31. The method of any one of clauses 28 to 30 wherein controlling the detrimental effect of *E. coli, Salmonella*, and/or *Campylobacter* comprises inhibiting *E. coli, Salmonella*, and/or *Campylobacter* disease in the animal.
32. The method of any one of clauses 28 to 30 wherein controlling the detrimental effect of *E. coli, Salmonella*, and/or *Campylobacter* comprises reducing *E. coli, Salmonella*, and/or *Campylobacter* disease in the animal.
33. The method of clause 29 wherein the animal is a porcine species and the porcine species is selected from the group consisting of a grow finish pig, a nursery pig, a sow, and a breeding stock pig.
34. The method of any one of clauses 28 to 33 wherein the *Bacillus* strain produces an enzyme selected from the group consisting of an α-galactosidase, a protease, a lipase, an amylase, a xylanase, a cellulase, and combinations thereof.
35. The method of any one of clauses 28 to 34 further comprising the step of administering to the animal another bacterial strain selected from the group consisting of another *Bacillus* strain, a lactic acid bacterial strain, and combinations thereof.
36. The method of any one of clauses 28 to 35 wherein the strain administered is *Bacillus* strain A12 (NRRL No.

B67516) or a strain having all of the identifying characteristics of *Bacillus* strain A12 (NRRL No. B67516).
37. The method of any one of clauses 28 to 35 wherein the strain administered is *Bacillus* strain 54 (NRRL No. B67517) or a strain having all of the identifying characteristics of *Bacillus* strain 54 (NRRL No. B67517).
38. The method of any one of clauses 28 to 35 wherein the strain administered is *Bacillus* strain 681 (NRRL No. B67515) or a strain having all of the identifying characteristics of *Bacillus* strain 681 (NRRL No. B67515).
39. The method of any one of clauses 28 to 35 wherein the strain administered is *Bacillus* strain 721 (NRRL No. B67514) or a strain having all of the identifying characteristics of *Bacillus* strain 721 (NRRL No. B67514).
40. The method of any one of clauses 28 to 39 wherein the *Bacillus* strain is administered in the feed composition at a dose of about $1.0 \times 10^3$ CFU/gram of the feed composition to about $5.0 \times 10^{12}$ CFU/gram of the feed composition.
41. The method of any one of clauses 28 to 40 wherein the *Bacillus* strain is administered in the feed composition at a dose of about $1.0 \times 10^3$ CFU/gram of the feed composition to about $1.0 \times 10^7$ CFU/gram of the feed composition.
42. The method of any one of clauses 28 to 41 wherein the *Bacillus* strain is administered in the feed composition at a dose greater than about $7.0 \times 10^4$ CFU/gram of the feed composition.
43. The method of any one of clauses 28 to 42 wherein the *Bacillus* strain is administered in the feed composition at a dose of about $7.3 \times 10^4$ CFU/gram of the feed composition.
44. The method of any one of clauses 28 to 43 wherein the *Bacillus* strain is isolated from a high performing grow finish pig.
45. The method of any one of clauses 28 to 44 further comprising the step of administering an antibiotic to the animal.
46. The method of any one of clauses 28 to 45 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
47. The method of clause 46 wherein the enzyme is an NSPase or a phytase.
48. The method of any one of clauses 28 to 47 wherein controlling the detrimental effect of *E. coli* comprises maintaining the microbial balance in the animal.
49. The method of clause 29 wherein the animal is a companion animal.
50. The method of clause 49 wherein the animal is a canine species or a feline species.
51. The method of clause 29 wherein the animal is a sow and the *Bacillus* strain is administered during lactation.
52. The method of clause 29 wherein the animal is a sow and the *Bacillus* strain is administered during gestation.
53. The method of any one of clauses 28 to 52 wherein the feed composition is administered daily to the animal.
54. The method of clause 28 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.
55. A commercial package comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
56. A feed additive for an animal feed comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
57. An additive for the drinking water of an animal comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
58. An animal feed composition comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
59. The commercial package, feed additive, feed composition, or additive for the drinking water of the animal of any one of clauses 55 to 58 wherein the *Bacillus* strain causes an effect selected from the group consisting of preventing *E. coli*, *Salmonella*, and/or *Campylobacter* disease, reducing *E. coli*, *Salmonella*, and/or *Campylobacter* disease, maintaining the microbial balance of the animal, and combinations thereof.
60. The commercial package, feed additive, feed composition, or additive for the drinking water of the animal of any one of clauses 55 to 59, wherein the *Bacillus* strain reduces *E. coli*, *Salmonella*, and/or *Campylobacter* disease in the animal.
61. The feed additive or additive for the drinking water of the animal of clause 56 or 57 in the form of a concentrate.
62. The feed additive or additive for the drinking water of the animal of clause 56 or 57 in the form of a super-concentrate.

63. The feed additive, feed composition, or additive for the drinking water of the animal of any one of clauses 56 to 62 in dry form.
64. The feed composition of clause 63 in pelleted form.
65. The commercial package of clause 55 wherein the strains are in a form selected from the group consisting of a powder, a liquid, and a pellet form.
66. The commercial package, feed additive, additive for the drinking water of the animal, or feed composition of any one of clauses 55 to 65 further comprising a carrier for the *Bacillus* strains.
67. The commercial package, feed additive, additive for the drinking water of the animal, or feed composition of clause 66 wherein the carrier is selected from the group consisting of a bran, rice hulls, a salt, a dextrin, and combinations thereof.
68. The commercial package, feed additive, additive for the drinking water of the animal, or feed composition of any one of clauses 55 to 67 in a bag.
69. The commercial package, feed additive, additive for the drinking water of the animal, or feed composition of clause 68 wherein the bag is a plastic bag.
70. The commercial package, feed additive, additive for the drinking water of the animal, or feed composition of any one of clauses 55 to 69 further comprising instructions for use of one or more of the *Bacillus* strains.
71. The commercial package, feed additive, feed composition, or additive for the drinking water of the animal of any one of clauses 68 to 70 in a 20-pound bag.
72. The commercial package, feed additive, feed composition, or additive for the drinking water of the animal of any one of clauses 68 to 70 in a 50-pound bag.
73. The feed additive or additive for the drinking water of the animal of any one of clauses 56, 57, 59 to 63, or 66 to 72 in powder form.
74. The feed additive or additive for the drinking water of the animal of any one of clauses 56, 57, 59 to 60, or 68 to 70 in liquid form.
75. The commercial package, feed additive, additive for the drinking water of the animal, or feed composition of any one of clauses 55 to 74 in a container for commercial use.
76. The commercial package, feed additive, additive for the drinking water of the animal, or feed composition of clause 75 wherein the container comprises plastic.
77. The commercial package, feed additive, additive for the drinking water of the animal, or feed composition of clause 75 wherein the container comprises paper.
78. The commercial package, feed additive, additive for the drinking water of the animal, or feed composition of any one of clauses 55 to 77 further comprising a binder.
79. The commercial package, feed additive, additive for the drinking water of the animal, or feed composition of clause 78 wherein the binder is selected from the group consisting of clay, yeast cell wall components, aluminum silicate, and glucan, or combinations thereof.
80. A method of feeding an animal, the method comprising the step of administering to the animal a feed composition or drinking water comprising an effective amount of an additive comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
81. The method of clause 80 wherein the animal is selected from the group consisting of a poultry species, a porcine species, a caprine species, a bovine species, an ovine species, an equine species, and a companion animal.
82. The method of clause 81 wherein the poultry species is a broiler chicken.
83. The method of any one of clauses 80 to 82 wherein the strain causes *E. coli*, *Salmonella*, and/or *Campylobacter* inhibition which prevents *E. coli*, *Salmonella*, and/or *Campylobacter* disease in the animal.
84. The method of any one of clauses 80 to 82 wherein the strain causes *E. coli*, *Salmonella*, and/or *Campylobacter* inhibition which reduces *E. coli*, *Salmonella*, and/or *Campylobacter* disease in the animal.
85. The method of clause 81 wherein the animal is a porcine species and the porcine species is selected from the group consisting of a grow finish pig, a nursery pig, a sow, and a breeding stock pig.
86. The method of any one of clauses 80 to 85 wherein the *Bacillus* strain produces an enzyme selected from the group consisting of an α-galactosidase, a protease, a lipase, an amylase, a xylanase, a cellulase, and combinations thereof.
87. The method of any one of clauses 80 to 86 further comprising the step of administering to the animal another bacterial strain selected from the group consisting of another *Bacillus* strain, a lactic acid bacterial strain, and combinations thereof.
88. The method of any one of clauses 80 to 87 wherein the strain administered is *Bacillus* strain A12 (NRRL No. B67516) or a strain having all of the identifying characteristics of *Bacillus* strain A12 (NRRL No. B67516).
89. The method of any one of clauses 80 to 87 wherein the strain administered is *Bacillus* strain 54 (NRRL No. B67517) or a strain having all of the identifying characteristics of *Bacillus* strain 54 (NRRL No. B67517).
90. The method of any one of clauses 80 to 87 wherein the strain administered is *Bacillus* strain 681 (NRRL No. B67515) or a strain having all of the identifying characteristics of *Bacillus* strain 681 (NRRL No. B67515).
91. The method of any one of clauses 80 to 87 wherein the strain administered is *Bacillus* strain 721 (NRRL No. B67514) or a strain having all of the identifying characteristics of *Bacillus* strain 721 (NRRL No. B67514).
92. The method of any one of clauses 80 to 91 wherein the *Bacillus* strain is administered in the feed composition at a dose of about $1.0 \times 10^3$ CFU/gram of the feed composition to about $5.0 \times 10^{12}$ CFU/gram of the feed composition.
93. The method of any one of clauses 80 to 92 wherein the *Bacillus* strain is administered in the feed composition at a dose of about $1.0 \times 10^3$ CFU/gram of the feed composition to about $1.0 \times 10^7$ CFU/gram of the feed composition.
94. The method of any one of clauses 80 to 93 wherein the *Bacillus* strain is administered in the feed composition at a dose greater than about $7.0 \times 10^4$ CFU/gram of the feed composition.

95. The method of any one of clauses 80 to 94 wherein the *Bacillus* strain is administered in the feed composition at a dose of about $7.3 \times 10^4$ CFU/gram of the feed composition.
96. The method of any one of clauses 80 to 95 wherein the *Bacillus* strain is isolated from a high performing grow finish pig.
97. The method of any one of clauses 80 to 96 further comprising the step of administering an antibiotic to the animal.
98. The method of any one of clauses 80 to 97 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
99. The method of clause 98 wherein the enzyme is an NSPase or a phytase.
100. The method of any one of clauses 80 to 99 wherein the microbial balance in the animal is maintained.
101. The method of clause 81 wherein the animal is a companion animal.
102. The method of clause 101 wherein the animal is a canine species or a feline species.
103. The method of clause 81 wherein the animal is a sow and the *Bacillus* strain is administered during lactation.
104. The method of clause 81 wherein the animal is a sow and the *Bacillus* strain is administered during gestation.
105. The method of any one of clauses 80 to 104 wherein the feed composition is administered daily to the animal.
106. The method of clause 80 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.
107. The method, commercial package, feed additive, additive for the drinking water of the animal, or feed composition or of any one of clauses 1 to 106 wherein the strain administered is *Bacillus* strain A12 (NRRL No. B67516).
108. The method, commercial package, feed additive, additive for the drinking water of the animal, or feed composition of any one of clauses 1 to 106 wherein the strain administered is *Bacillus* strain 54 (NRRL No. B67517).
109. The method, commercial package, feed additive, additive for the drinking water of the animal, or feed composition of any one of clauses 1 to 106 wherein the strain administered is *Bacillus* strain 681 (NRRL No. B67515).
110. The method, commercial package, feed additive, additive for the drinking water of the animal, or feed composition of any one of clauses 1 to 106 wherein the strain administered is *Bacillus* strain 721 (NRRL No. B67514).
111. The method of any one of clauses 1 to 8, 28 to 35, or 80 to 87 wherein isolated *Bacillus* strains selected from the group consisting of *Bacillus* strain A12 (NRRL No. B67516), 54 (NRRL No. B67517), 681 (NRRL No. B67515), 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), and a strain having all of the identifying characteristics of *Bacillus* strain 721 (NRRL No. B67514) are administered in combination in a single composition.
112. The method of any one of clauses 1 to 8, 28 to 35, or 80 to 87 wherein isolated *Bacillus* strains selected from the group consisting of *Bacillus* strain A12 (NRRL No. B67516), 54 (NRRL No. B67517), 681 (NRRL No. B67515), 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), and a strain having all of the identifying characteristics of *Bacillus* strain 721 (NRRL No. B67514) are administered in combination in separate compositions.
113. The method, commercial package, feed additive, feed composition, or additive for drinking water of any one of clauses 1 to 112 wherein the *Bacillus* strain has an effect selected from the group consisting of maintaining microbial balance in the gut of the animal, preventing or reducing *E. coli, Salmonella*, and/or *Campylobacter* disease in the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal.
114. A method of feeding an animal, the method comprising the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain prevents or reduces prolapse in the animal.
115. A method of controlling a detrimental effect of *E. coli* and/or *Campylobacter*, the method comprising the steps of administering to an animal a feed composition or drinking water comprising an effective amount of an additive comprising an isolated *Bacillus* strain selected from the group consisting of *Bacillus* strain A12

(NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, and controlling the detrimental effect of *E. coli* and/or *Campylobacter* in the animal wherein the detrimental effect is prolapse in the animal.

116. The method of clause 114 or 115, wherein the animal is selected from the group consisting of a porcine species, a caprine species, a bovine species, an ovine species, an equine species, and a companion animal.

117. The method of clause 116, wherein the animal is a porcine species and the porcine species is selected from the group consisting of a grow finish pig, a sow, a nursery pig, and a breeding stock pig.

118. The method of clause 117, wherein the animal is a sow.

119. The method of any one of clauses 114 to 118, wherein the detrimental effect is a detrimental effect of *Campylobacter*.

120. The method of clause 119, wherein the *Campylobacter* is *C. coli*.

121. The method of any one of clauses 114 to 120 wherein the *Bacillus* strain produces an enzyme selected from the group consisting of an α-galactosidase, a protease, a lipase, an amylase, a xylanase, a cellulase, and combinations thereof.

122. The method of any one of clauses 114 to 121 further comprising the step of administering to the animal another bacterial strain selected from the group consisting of another *Bacillus* strain, a lactic acid bacterial strain, and combinations thereof.

123. The method of any one of clauses 114 to 122 wherein the strain administered is *Bacillus* strain A12 (NRRL No. B67516).

124. The method of any one of clauses 114 to 122 wherein the strain administered is *Bacillus* strain 54 (NRRL No. B67517).

125. The method of any one of clauses 114 to 122 wherein the strain administered is *Bacillus* strain 681 (NRRL No. B67515).

126. The method of any one of clauses 114 to 122 wherein the strain administered is *Bacillus* strain 721 (NRRL No. B67514).

127. The method of any one of clauses 114 to 122 wherein the strain administered is *Bacillus* strain 300 (NRRL No. B-50943).

128. The method of any one of clauses 114 to 122 wherein the strain administered is *Bacillus* strain 101 (NRRL No. B-67218).

129. The method of any one of clauses 114 to 122 wherein the strain administered is *Bacillus* strain 235 (NRRL No. B-67219).

130. The method of any one of clauses 114 to 122 wherein the strain administered is *Bacillus* strain 86 (NRRL No. B-50944).

131. The method of any one of clauses 114 to 122 wherein the strain administered is *Bacillus* strain 102 (NRRL No. B-67276).

132. The method of any one of clauses 114 to 122 wherein the strain administered is *Bacillus* strain 177 ((NRRL No. B-67275).

133. The method of any one of clauses 114 to 132 further comprising the step of administering an antibiotic to the animal.

134. The method of any one of clauses 114 to 133 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

135. The method of any one of clauses 114 to 134 wherein the *Bacillus* strain is administered during lactation.

136. The method of any one of clauses 114 to 134 wherein the *Bacillus* strain is administered during gestation.

137. The method of any one of clauses 114 to 136 wherein the feed composition is administered daily to the animal.

138. The method of any one of clauses 114 to 137 wherein the prolapse is vaginal and/or uterine prolapse.

139. The method of any one of clauses 114 to 137 wherein the prolapse is rectal and/or anal prolapse.

140. The method of any one of clauses 114 to 139 wherein the feed is administered in the form of ground meal.

141. A method of feeding an animal, the method comprising the step of administering to the animal a feed composition or drinking water comprising an effective amount of an additive comprising an isolated bacterial strain, or combinations thereof, wherein the bacterial strain prevents or reduces prolapse in the animal.

142. A method of controlling an effect of detrimental bacteria, the method comprising the steps of administering to an animal a feed composition or drinking water comprising an effective amount of an additive comprising an isolated bacterial strain, or combinations thereof, different than the detrimental bacteria, and controlling the effect of the detrimental bacteria wherein the detrimental effect is prolapse in the animal.

143. The method of clause 141 or 142, wherein the animal is selected from the group consisting of a porcine species, a caprine species, a bovine species, an ovine species, an equine species, and a companion animal.

144. The method of clause 143 wherein the animal is a porcine species and the porcine species is selected from the group consisting of a grow finish pig, a sow, a nursery pig, and a breeding stock pig.

145. The method of clause 143, wherein the animal is a sow.

146. The method of any one of clauses 141 to 145 wherein the bacterial strain produces an enzyme selected from the group consisting of an α-galactosidase, a protease, a lipase, an amylase, a xylanase, a cellulase, and combinations thereof.

147. The method of any one of clauses 141 to 146 further comprising the step of administering an antibiotic to the animal.
148. The method of any one of clauses 141 to 147 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
149. The method of any one of clauses 141 to 148 wherein the bacterial strain is administered during lactation.
150. The method of any one of clauses 141 to 148 wherein the bacterial strain is administered during gestation.
151. The method of any one of clauses 141 to 150 wherein the feed composition is administered daily to the animal.
152. The method of any one of clauses 141 to 151 wherein the prolapse is vaginal and/or uterine prolapse.
153. The method of any one of clauses 141 to 151 wherein the prolapse is rectal and/or anal prolapse.
154. The method of any one of clauses 141 to 153 wherein the feed is administered in the form of ground meal.
155. The method of any one of clauses 141 to 154 wherein the microbes in the gut of the animal are altered to reduce prolapse.
156. A method of feeding an animal, comprising the step of administering to the animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, wherein the *Bacillus* strain causes *Campylobacter* inhibition in the animal.
157. A method of controlling a detrimental effect of *Campylobacter*, the method comprising the steps of administering to an animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, and controlling the detrimental effect of *Campylobacter* in the animal.
158. The method of clause 156 or 157 wherein the animal is selected from the group consisting of a poultry species, a porcine species, a caprine species, a bovine species, an ovine species, an equine species, and a companion animal.
159. The method of clause 158 wherein the poultry species is a broiler chicken.
160. The method of clause 156 wherein *Campylobacter* inhibition prevents *Campylobacter* disease in the animal.
161. The method of clause 156 wherein the *Campylobacter* inhibition reduces *Campylobacter* disease in the animal.
162. The method of clause 158 wherein the animal is a porcine species and the porcine species is selected from the group consisting of a grow finish pig, a nursery pig, a sow, and a breeding stock pig.
163. The method of any one of clauses 156 to 162 wherein the *Bacillus* strain produces an enzyme selected from the group consisting of an α-galactosidase, a protease, a lipase, an amylase, a xylanase, a cellulase, and combinations thereof.
164. The method of any one of clauses 156 to 163 further comprising the step of administering to the animal another bacterial strain selected from the group consisting of another *Bacillus* strain, a lactic acid bacterial strain, and combinations thereof.
165. The method of any one of clauses 156 to 164 wherein the strain administered is *Bacillus* strain 101 (NRRL No. B-67218).
166. The method of any one of clauses 156 to 164 wherein the strain administered is *Bacillus* strain 235 (NRRL No. B-67219).
167. The method of any one of clauses 156 to 166 wherein the *Bacillus* strain is administered in the feed composition at a dose of about $1.0 \times 10^3$ CFU/gram of the feed composition to about $5.0 \times 10^{12}$ CFU/gram of the feed composition.
168. The method of any one of clauses 156 to 166 wherein the *Bacillus* strain is administered in the feed composition at a dose of about $1.0 \times 10^3$ CFU/gram of the feed composition to about $1.0 \times 10^7$ CFU/gram of the feed composition.
169. The method of any one of clauses 156 to 166 wherein the *Bacillus* strain is administered in the feed composition at a dose greater than about $7.0 \times 10^4$ CFU/gram of the feed composition.
170. The method of any one of clauses 156 to 169 further comprising the step of administering an antibiotic to the animal.
171. The method of any one of clauses 156 to 170 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
172. The method of clause 171 wherein the enzyme is an NSPase or a phytase.
173. The method of clause 158 wherein the animal is a sow and the *Bacillus* strain is administered during lactation.
174. The method of clause 158 wherein the animal is a sow and the *Bacillus* strain is administered during gestation.
175. The method of any one of clauses 156 to 174 wherein the feed composition is administered daily to the animal.
176. The method of clause 158 wherein the animal is selected from the group consisting of a chicken, a pig, a horse, a pony, a cow, a turkey, a goat, a sheep, a quail, a pheasant, an ostrich, a duck, and combinations thereof.

BRIEF DESCRIPTION OF THE DRAWINGS

FIG. 1A shows the results of whole cell preparation of 681 and 721 for efficacy against various isolates of *Salmonella*. FIG. 1B shows the results of whole cell preparation of 681 and 721 for efficacy against various isolates of *Campylobacter*. FIG. 1C shows the results of whole cell preparation of 681 and 721 for efficacy against various isolates of *Escherichia coli*.

FIG. 2A shows data acquired from A12 and 54, against a sub sample of 110 *E. coli* isolates. FIG. 2B shows data acquired from A12 and 54 strains against 48 susceptible *E. coli* isolates. FIG. 2C shows data acquired from the A12 and 54, against 3 *Salmonella* isolates.

FIG. 5 shows growth inhibition in millimeters of *Campylobacter* field isolates by *Bacillus* strains determined by cross streak assay. *Campylobacter* isolates were acquired from prolapse animals (B9-H12) and additional sick animals (A1-D3).

DETAILED DESCRIPTION OF ILLUSTRATIVE EMBODIMENTS

Figure 3A:
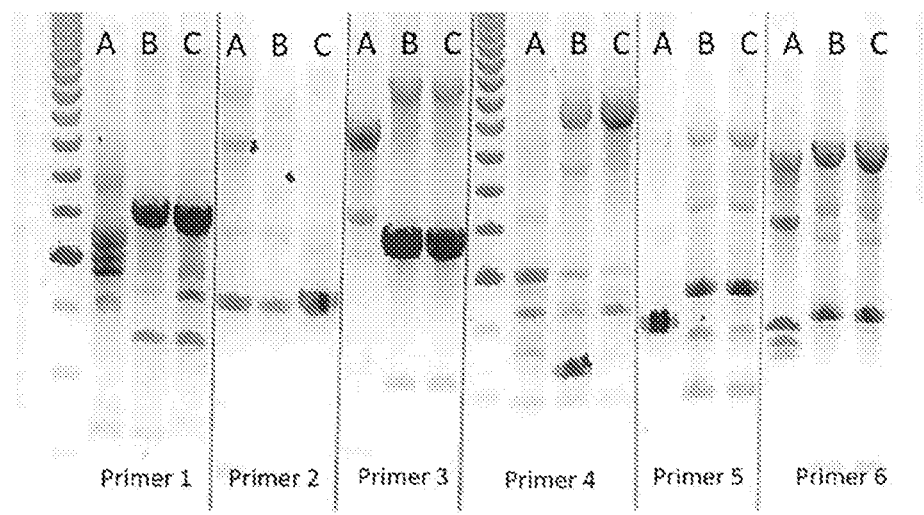
FIG. 3A shows the RAPD testing results for the 681 and 721 strains.

Methods and compositions are provided for inhibiting *E. coli* in animals, such as agricultural animals. In various embodiments, the compositions for use in the methods described herein can be a commercial package, a feed additive for an animal feed composition, an additive for the drinking water of an animal, or an animal feed composition (e.g., a complete feed), each comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.

In one embodiment of the methods described herein, a method is provided of feeding an animal. The method comprises the step of administering to the animal a feed composition or drinking water comprising an effective amount of an additive comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, wherein the *Bacillus* strain causes *E. coli, Salmonella*, and/or *Campylobacter* inhibition in the animal.

In another embodiment of the methods described herein, a method is provided of feeding an animal. The method comprises the step of administering to the animal a feed composition or drinking water comprising an effective amount of an additive comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.

In another embodiment of the methods described herein, a method is provided of controlling a detrimental effect of *E. coli, Salmonella*, and/or *Campylobacter*. The method comprises the steps of administering to an animal a feed composition or drinking water comprising an effective amount of an additive comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, and controlling the detrimental effect of *E. coli, Salmonella*, and/or *Campylobacter* in the animal.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No.

B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain prevents or reduces prolapse in the animal.

In still another embodiment, a method of controlling a detrimental effect of *E. coli* and/or *Campylobacter* is provided. The method comprises the steps of administering to an animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, and controlling the detrimental effect of *E. coli* and/or *Campylobacter* in the animal wherein the detrimental effect is prolapse in the animal.

In another embodiment of the methods described herein, a method is provided of feeding an animal. The method comprises the step of administering to the animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, wherein the *Bacillus* strain causes *Campylobacter* inhibition in the animal.

In another embodiment of the methods described herein, a method is provided of controlling a detrimental effect of *Campylobacter*. The method comprises the steps of administering to an animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, and controlling the detrimental effect of *Campylobacter* in the animal.

The following clauses, and combinations thereof, provide various additional illustrative aspects of the invention described herein. The various embodiments described in this section titled "DETAILED DESCRIPTION OF ILLUSTRATIVE EMBODIMENTS" are applicable to any of the following embodiments of the invention described in the numbered clauses below.

1. A method of feeding an animal, the method comprising the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, wherein the *Bacillus* strain causes *E. coli*, *Salmonella*, and/or *Campylobacter* inhibition in the animal.
2. The method of clause 1 wherein the animal is selected from the group consisting of a poultry species, a porcine species, a caprine species, a bovine species, an ovine species, an equine species, and a companion animal.
3. The method of clause 2 wherein the poultry species is a broiler chicken.
4. The method of any one of clauses 1 to 3 wherein the *E. coli*, *Salmonella*, and/or *Campylobacter* inhibition prevents *E. coli*, *Salmonella*, and/or *Campylobacter* disease in the animal.
5. The method of any one of clauses 1 to 3 wherein the *E. coli*, *Salmonella*, and/or *Campylobacter* inhibition reduces *E. coli*, *Salmonella*, and/or *Campylobacter* disease in the animal.
6. The method of clause 2 wherein the animal is a porcine species and the porcine species is selected from the group consisting of a grow finish pig, a nursery pig, a sow, and a breeding stock pig.
7. The method of any one of clauses 1 to 6 wherein the *Bacillus* strain produces an enzyme selected from the group consisting of an α-galactosidase, a protease, a lipase, an amylase, a xylanase, a cellulase, and combinations thereof.
8. The method of any one of clauses 1 to 7 further comprising the step of administering to the animal another bacterial strain selected from the group consisting of another *Bacillus* strain, a lactic acid bacterial strain, and combinations thereof.
9. The method of any one of clauses 1 to 8 wherein the strain administered is *Bacillus* strain A12 (NRRL No. B67516) or a strain having all of the identifying characteristics of *Bacillus* strain A12 (NRRL No. B67516).
10. The method of any one of clauses 1 to 8 wherein the strain administered is *Bacillus* strain 54 (NRRL No.

B67517) or a strain having all of the identifying characteristics of *Bacillus* strain 54 (NRRL No. B67517).
11. The method of any one of clauses 1 to 8 wherein the strain administered is *Bacillus* strain 681 (NRRL No. B67515) or a strain having all of the identifying characteristics of *Bacillus* strain 681 (NRRL No. B67515).
12. The method of any one of clauses 1 to 8 wherein the strain administered is *Bacillus* strain 721 (NRRL No. B67514) or a strain having all of the identifying characteristics of *Bacillus* strain 721 (NRRL No. B67514).
13. The method of any one of clauses 1 to 12 wherein the *Bacillus* strain is administered in the feed composition at a dose of about $1.0 \times 10^3$ CFU/gram of the feed composition to about $5.0 \times 10^{12}$ CFU/gram of the feed composition.
14. The method of any one of clauses 1 to 12 wherein the *Bacillus* strain is administered in the feed composition at a dose of about $1.0 \times 10^3$ CFU/gram of the feed composition to about $1.0 \times 10^7$ CFU/gram of the feed composition.
15. The method of any one of clauses 1 to 14 wherein the *Bacillus* strain is administered in the feed composition at a dose greater than about $7.0 \times 10^4$ CFU/gram of the feed composition.
16. The method of any one of clauses 1 to 15 wherein the *Bacillus* strain is administered in the feed composition at a dose of about $7.3 \times 10^4$ CFU/gram of the feed composition.
17. The method of any one of clauses 1 to 16 wherein the *Bacillus* strain is isolated from a high performing grow finish pig.
18. The method of any one of clauses 1 to 17 further comprising the step of administering an antibiotic to the animal.
19. The method of any one of clauses 1 to 18 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
20. The method of clause 19 wherein the enzyme is an NSPase or a phytase.
21. The method of any one of clauses 1 to 20 wherein the microbial balance in the animal is maintained.
22. The method of clause 2 wherein the animal is a companion animal.
23. The method of clause 22 wherein the animal is a canine species or a feline species.
24. The method of clause 2 wherein the animal is a sow and the *Bacillus* strain is administered during lactation.
25. The method of clause 2 wherein the animal is a sow and the *Bacillus* strain is administered during gestation.
26. The method of any one of clauses 1 to 25 wherein the feed composition is administered daily to the animal.
27. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.
28. A method of controlling a detrimental effect of *E. coli, Salmonella*, and/or *Campylobacter*, the method comprising the steps of administering to an animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, and controlling the detrimental effect of *E. coli, Salmonella*, and/or *Campylobacter* in the animal.
29. The method of clause 28 wherein the animal is selected from the group consisting of a poultry species, a porcine species, a caprine species, a bovine species, an ovine species, an equine species, and a companion animal.
30. The method of clause 29 wherein the poultry species is a broiler chicken.
31. The method of any one of clauses 28 to 30 wherein controlling the detrimental effect of *E. coli, Salmonella*, and/or *Campylobacter* comprises inhibiting *E. coli, Salmonella*, and/or *Campylobacter* disease in the animal.
32. The method of any one of clauses 28 to 30 wherein controlling the detrimental effect of *E. coli, Salmonella*, and/or *Campylobacter* comprises reducing *E. coli, Salmonella*, and/or *Campylobacter* disease in the animal.
33. The method of clause 29 wherein the animal is a porcine species and the porcine species is selected from the group consisting of a grow finish pig, a nursery pig, a sow, and a breeding stock pig.
34. The method of any one of clauses 28 to 33 wherein the *Bacillus* strain produces an enzyme selected from the group consisting of an α-galactosidase, a protease, a lipase, an amylase, a xylanase, a cellulase, and combinations thereof.
35. The method of any one of clauses 28 to 34 further comprising the step of administering to the animal another bacterial strain selected from the group consisting of another *Bacillus* strain, a lactic acid bacterial strain, and combinations thereof.
36. The method of any one of clauses 28 to 35 wherein the strain administered is *Bacillus* strain A12 (NRRL No. B67516) or a strain having all of the identifying characteristics of *Bacillus* strain A12 (NRRL No. B67516).
37. The method of any one of clauses 28 to 35 wherein the strain administered is *Bacillus* strain 54 (NRRL No. B67517) or a strain having all of the identifying characteristics of *Bacillus* strain 54 (NRRL No. B67517).
38. The method of any one of clauses 28 to 35 wherein the strain administered is *Bacillus* strain 681 (NRRL No. B67515) or a strain having all of the identifying characteristics of *Bacillus* strain 681 (NRRL No. B67515).
39. The method of any one of clauses 28 to 35 wherein the strain administered is *Bacillus* strain 721 (NRRL No. B67514) or a strain having all of the identifying characteristics of *Bacillus* strain 721 (NRRL No. B67514).
40. The method of any one of clauses 28 to 39 wherein the *Bacillus* strain is administered in the feed composition at a dose of about $1.0 \times 10^3$ CFU/gram of the feed composition to about $5.0 \times 10^{12}$ CFU/gram of the feed composition.
41. The method of any one of clauses 28 to 40 wherein the *Bacillus* strain is administered in the feed composition at a dose of about $1.0 \times 10^3$ CFU/gram of the feed composition to about $1.0 \times 10^7$ CFU/gram of the feed composition.

42. The method of any one of clauses 28 to 41 wherein the *Bacillus* strain is administered in the feed composition at a dose greater than about $7.0 \times 10^4$ CFU/gram of the feed composition.
43. The method of any one of clauses 28 to 42 wherein the *Bacillus* strain is administered in the feed composition at a dose of about $7.3 \times 10^4$ CFU/gram of the feed composition.
44. The method of any one of clauses 28 to 43 wherein the *Bacillus* strain is isolated from a high performing grow finish pig.
45. The method of any one of clauses 28 to 44 further comprising the step of administering an antibiotic to the animal.
46. The method of any one of clauses 28 to 45 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
47. The method of clause 46 wherein the enzyme is an NSPase or a phytase.
48. The method of any one of clauses 28 to 47 wherein controlling the detrimental effect of *E. coli* comprises maintaining the microbial balance in the animal.
49. The method of clause 29 wherein the animal is a companion animal.
50. The method of clause 49 wherein the animal is a canine species or a feline species.
51. The method of clause 29 wherein the animal is a sow and the *Bacillus* strain is administered during lactation.
52. The method of clause 29 wherein the animal is a sow and the *Bacillus* strain is administered during gestation.
53. The method of any one of clauses 28 to 52 wherein the feed composition is administered daily to the animal.
54. The method of clause 28 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.
55. A commercial package comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
56. A feed additive for an animal feed comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
57. An additive for the drinking water of an animal comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
58. An animal feed composition comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
59. The commercial package, feed additive, feed composition, or additive for the drinking water of the animal of any one of clauses 55 to 58 wherein the *Bacillus* strain causes an effect selected from the group consisting of preventing *E. coli*, *Salmonella*, and/or *Campylobacter* disease, reducing *E. coli*, *Salmonella*, and/or *Campylobacter* disease, maintaining the microbial balance of the animal, and combinations thereof.
60. The commercial package, feed additive, feed composition, or additive for the drinking water of the animal of any one of clauses 55 to 59, wherein the *Bacillus* strain reduces *E. coli*, *Salmonella*, and/or *Campylobacter* disease in the animal.
61. The feed additive or additive for the drinking water of the animal of clause 56 or 57 in the form of a concentrate.
62. The feed additive or additive for the drinking water of the animal of clause 56 or 57 in the form of a super-concentrate.
63. The feed additive, feed composition, or additive for the drinking water of the animal of any one of clauses 56 to 62 in dry form.
64. The feed composition of clause 63 in pelleted form.
65. The commercial package of clause 55 wherein the strains are in a form selected from the group consisting of a powder, a liquid, and a pellet form.
66. The commercial package, feed additive, additive for the drinking water of the animal, or feed composition of any one of clauses 55 to 65 further comprising a carrier for the *Bacillus* strains.
67. The commercial package, feed additive, additive for the drinking water of the animal, or feed composition of clause 66 wherein the carrier is selected from the group consisting of a bran, rice hulls, a salt, a dextrin, and combinations thereof.
68. The commercial package, feed additive, additive for the drinking water of the animal, or feed composition of any one of clauses 55 to 67 in a bag.
69. The commercial package, feed additive, additive for the drinking water of the animal, or feed composition of clause 68 wherein the bag is a plastic bag.
70. The commercial package, feed additive, additive for the drinking water of the animal, or feed composition of any one of clauses 55 to 69 further comprising instructions for use of one or more of the *Bacillus* strains.
71. The commercial package, feed additive, feed composition, or additive for the drinking water of the animal of any one of clauses 68 to 70 in a 20-pound bag.
72. The commercial package, feed additive, feed composition, or additive for the drinking water of the animal of any one of clauses 68 to 70 in a 50-pound bag.
73. The feed additive or additive for the drinking water of the animal of any one of clauses 56, 57, 59 to 63, or 66 to 72 in powder form.
74. The feed additive or additive for the drinking water of the animal of any one of clauses 56, 57, 59 to 60, or 68 to 70 in liquid form.
75. The commercial package, feed additive, additive for the drinking water of the animal, or feed composition of any one of clauses 55 to 74 in a container for commercial use.
76. The commercial package, feed additive, additive for the drinking water of the animal, or feed composition of clause 75 wherein the container comprises plastic.
77. The commercial package, feed additive, additive for the drinking water of the animal, or feed composition of clause 75 wherein the container comprises paper.
78. The commercial package, feed additive, additive for the drinking water of the animal, or feed composition of any one of clauses 55 to 77 further comprising a binder.
79. The commercial package, feed additive, additive for the drinking water of the animal, or feed composition of clause 78 wherein the binder is selected from the group consisting of clay, yeast cell wall components, aluminum silicate, and glucan, or combinations thereof.
80. A method of feeding an animal, the method comprising the step of administering to the animal a feed composition or drinking water comprising an effective amount of an additive comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.
81. The method of clause 80 wherein the animal is selected from the group consisting of a poultry species, a porcine species, a caprine species, a bovine species, an ovine species, an equine species, and a companion animal.
82. The method of clause 81 wherein the poultry species is a broiler chicken.
83. The method of any one of clauses 80 to 82 wherein the strain causes *E. coli*, *Salmonella*, and/or *Campylobacter* inhibition which prevents *E. coli*, *Salmonella*, and/or *Campylobacter* disease in the animal.
84. The method of any one of clauses 80 to 82 wherein the strain causes *E. coli*, *Salmonella*, and/or *Campylobacter* inhibition which reduces *E. coli*, *Salmonella*, and/or *Campylobacter* disease in the animal.
85. The method of clause 81 wherein the animal is a porcine species and the porcine species is selected from the group consisting of a grow finish pig, a nursery pig, a sow, and a breeding stock pig.
86. The method of any one of clauses 80 to 85 wherein the *Bacillus* strain produces an enzyme selected from the group consisting of an α-galactosidase, a protease, a lipase, an amylase, a xylanase, a cellulase, and combinations thereof.
87. The method of any one of clauses 80 to 86 further comprising the step of administering to the animal another bacterial strain selected from the group consisting of another *Bacillus* strain, a lactic acid bacterial strain, and combinations thereof.
88. The method of any one of clauses 80 to 87 wherein the strain administered is *Bacillus* strain A12 (NRRL No. B67516) or a strain having all of the identifying characteristics of *Bacillus* strain A12 (NRRL No. B67516).
89. The method of any one of clauses 80 to 87 wherein the strain administered is *Bacillus* strain 54 (NRRL No. B67517) or a strain having all of the identifying characteristics of *Bacillus* strain 54 (NRRL No. B67517).
90. The method of any one of clauses 80 to 87 wherein the strain administered is *Bacillus* strain 681 (NRRL No. B67515) or a strain having all of the identifying characteristics of *Bacillus* strain 681 (NRRL No. B67515).
91. The method of any one of clauses 80 to 87 wherein the strain administered is *Bacillus* strain 721 (NRRL No. B67514) or a strain having all of the identifying characteristics of *Bacillus* strain 721 (NRRL No. B67514).
92. The method of any one of clauses 80 to 91 wherein the *Bacillus* strain is administered in the feed composition at a dose of about $1.0 \times 10^3$ CFU/gram of the feed composition to about $5.0 \times 10^{12}$ CFU/gram of the feed composition.
93. The method of any one of clauses 80 to 92 wherein the *Bacillus* strain is administered in the feed composition at a dose of about $1.0 \times 10^3$ CFU/gram of the feed composition to about $1.0 \times 10^7$ CFU/gram of the feed composition.
94. The method of any one of clauses 80 to 93 wherein the *Bacillus* strain is administered in the feed composition at a dose greater than about $7.0 \times 10^4$ CFU/gram of the feed composition.
95. The method of any one of clauses 80 to 94 wherein the *Bacillus* strain is administered in the feed composition at a dose of about $7.3 \times 10^4$ CFU/gram of the feed composition.
96. The method of any one of clauses 80 to 95 wherein the *Bacillus* strain is isolated from a high performing grow finish pig.
97. The method of any one of clauses 80 to 96 further comprising the step of administering an antibiotic to the animal.
98. The method of any one of clauses 80 to 97 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
99. The method of clause 98 wherein the enzyme is an NSPase or a phytase.
100. The method of any one of clauses 80 to 99 wherein the microbial balance in the animal is maintained.
101. The method of clause 81 wherein the animal is a companion animal.
102. The method of clause 101 wherein the animal is a canine species or a feline species.

103. The method of clause 81 wherein the animal is a sow and the *Bacillus* strain is administered during lactation.
104. The method of clause 81 wherein the animal is a sow and the *Bacillus* strain is administered during gestation.
105. The method of any one of clauses 80 to 104 wherein the feed composition is administered daily to the animal.
106. The method of clause 80 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.
107. The method, commercial package, feed additive, additive for the drinking water of the animal, or feed composition or of any one of clauses 1 to106 wherein the strain administered is *Bacillus* strain A12 (NRRL No. B67516).
108. The method, commercial package, feed additive, additive for the drinking water of the animal, or feed composition of any one of clauses 1 to 106 wherein the strain administered is *Bacillus* strain 54 (NRRL No. B67517).
109. The method, commercial package, feed additive, additive for the drinking water of the animal, or feed composition of any one of clauses 1 to 106 wherein the strain administered is *Bacillus* strain 681 (NRRL No. B67515).
110. The method, commercial package, feed additive, additive for the drinking water of the animal, or feed composition of any one of clauses 1 to 106 wherein the strain administered is *Bacillus* strain 721 (NRRL No. B67514).
111. The method of any one of clauses 1 to 8, 28 to 35, or 80 to 87 wherein isolated *Bacillus* strains selected from the group consisting of *Bacillus* strain A12 (NRRL No. B67516), 54 (NRRL No. B67517), 681 (NRRL No. B67515), 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), and a strain having all of the identifying characteristics of *Bacillus* strain 721 (NRRL No. B67514) are administered in combination in a single composition.
112. The method of any one of clauses 1 to 8, 28 to 35, or 80 to 87 wherein isolated *Bacillus* strains selected from the group consisting of *Bacillus* strain A12 (NRRL No. B67516), 54 (NRRL No. B67517), 681 (NRRL No. B67515), 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), and a strain having all of the identifying characteristics of *Bacillus* strain 721 (NRRL No. B67514) are administered in combination in separate compositions.
113. The method, commercial package, feed additive, feed composition, or additive for drinking water of any one of clauses 1 to 112 wherein the *Bacillus* strain has an effect selected from the group consisting of maintaining microbial balance in the gut of the animal, preventing or reducing *E. coli*, *Salmonella*, and/or *Campylobacter* disease in the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal.
114. A method of feeding an animal, the method comprising the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain prevents or reduces prolapse in the animal.
115. A method of controlling a detrimental effect of *E. coli* and/or *Campylobacter*, the method comprising the steps of administering to an animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, and controlling the detrimental effect of *E. coli* and/or *Campylobacter* in the animal wherein the detrimental effect is prolapse in the animal.
116. The method of clause 114 or 115, wherein the animal is selected from the group consisting of a porcine species, a caprine species, a bovine species, an ovine species, an equine species, and a companion animal.
117. The method of clause 116, wherein the animal is a porcine species and the porcine species is selected from the group consisting of a grow finish pig, a sow, a nursery pig, and a breeding stock pig.
118. The method of clause 117, wherein the animal is a sow.
119. The method of any one of clauses 114 to 118, wherein the detrimental effect is a detrimental effect of *Campylobacter*.
120. The method of clause 119, wherein the *Campylobacter* is *C. coli*.
121. The method of any one of clauses 114 to 120 wherein the *Bacillus* strain produces an enzyme selected from the group consisting of an α-galactosidase, a protease, a lipase, an amylase, a xylanase, a cellulase, and combinations thereof.
122. The method of any one of clauses 114 to 121 further comprising the step of administering to the animal another bacterial strain selected from the group consisting of another *Bacillus* strain, a lactic acid bacterial strain, and combinations thereof.
123. The method of any one of clauses 114 to 122 wherein the strain administered is *Bacillus* strain A12 (NRRL No. B67516).
124. The method of any one of clauses 114 to 122 wherein the strain administered is *Bacillus* strain 54 (NRRL No. B67517).
125. The method of any one of clauses 114 to 122 wherein the strain administered is *Bacillus* strain 681 (NRRL No. B67515).
126. The method of any one of clauses 114 to 122 wherein the strain administered is *Bacillus* strain 721 (NRRL No. B67514).
127. The method of any one of clauses 114 to 122 wherein the strain administered is *Bacillus* strain 300 (NRRL No. B-50943).
128. The method of any one of clauses 114 to 122 wherein the strain administered is *Bacillus* strain 101 (NRRL No. B-67218).
129. The method of any one of clauses 114 to 122 wherein the strain administered is *Bacillus* strain 235 (NRRL No. B-67219).
130. The method of any one of clauses 114 to 122 wherein the strain administered is *Bacillus* strain 86 (NRRL No. B-50944).
131. The method of any one of clauses 114 to 122 wherein the strain administered is *Bacillus* strain 102 (NRRL No. B-67276).
132. The method of any one of clauses 114 to 122 wherein the strain administered is *Bacillus* strain 177 ((NRRL No. B-67275).
133. The method of any one of clauses 114 to 132 further comprising the step of administering an antibiotic to the animal.
134. The method of any one of clauses 114 to 133 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
135. The method of any one of clauses 114 to 134 wherein the *Bacillus* strain is administered during lactation.
136. The method of any one of clauses 114 to 134 wherein the *Bacillus* strain is administered during gestation.
137. The method of any one of clauses 114 to 136 wherein the feed composition is administered daily to the animal.
138. The method of any one of clauses 114 to 137 wherein the prolapse is vaginal and/or uterine prolapse.
139. The method of any one of clauses 114 to 137 wherein the prolapse is rectal and/or anal prolapse.
140. The method of any one of clauses 114 to 139 wherein the feed is administered in the form of ground meal.
141. A method of feeding an animal, the method comprising the step of administering to the animal a feed composition or drinking water comprising an effective amount of an additive comprising an isolated bacterial strain, or combinations thereof, wherein the bacterial strain prevents or reduces prolapse in the animal.
142. A method of controlling an effect of detrimental bacteria, the method comprising the steps of administering to an animal a feed composition or drinking water comprising an effective amount of an additive comprising an isolated bacterial strain, or combinations thereof, different than the detrimental bacteria, and controlling the effect of the detrimental bacteria wherein the detrimental effect is prolapse in the animal.
143. The method of clause 141 or 142, wherein the animal is selected from the group consisting of a porcine species, a caprine species, a bovine species, an ovine species, an equine species, and a companion animal.
144. The method of clause 143 wherein the animal is a porcine species and the porcine species is selected from the group consisting of a grow finish pig, a sow, a nursery pig, and a breeding stock pig.
145. The method of clause 143, wherein the animal is a sow.
146. The method of any one of clauses 141 to 145 wherein the bacterial strain produces an enzyme selected from the group consisting of an α-galactosidase, a protease, a lipase, an amylase, a xylanase, a cellulase, and combinations thereof.
147. The method of any one of clauses 141 to 146 further comprising the step of administering an antibiotic to the animal.
148. The method of any one of clauses 141 to 147 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
149. The method of any one of clauses 141 to 148 wherein the bacterial strain is administered during lactation.
150. The method of any one of clauses 141 to 148 wherein the bacterial strain is administered during gestation.
151. The method of any one of clauses 141 to 150 wherein the feed composition is administered daily to the animal.
152. The method of any one of clauses 141 to 151 wherein the prolapse is vaginal and/or uterine prolapse.
153. The method of any one of clauses 141 to 151 wherein the prolapse is rectal and/or anal prolapse.
154. The method of any one of clauses 141 to 153 wherein the feed is administered in the form of ground meal.
155. The method of any one of clauses 141 to 154 wherein the microbes in the gut of the animal are altered to reduce prolapse.

156. A method of feeding an animal, comprising the step of administering to the animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, wherein the *Bacillus* strain causes *Campylobacter* inhibition in the animal.

157. A method of controlling a detrimental effect of *Campylobacter*, the method comprising the steps of administering to an animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, and controlling the detrimental effect of *Campylobacter* in the animal.

158. The method of clause 156 or 157 wherein the animal is selected from the group consisting of a poultry species, a porcine species, a caprine species, a bovine species, an ovine species, an equine species, and a companion animal.

159. The method of clause 158 wherein the poultry species is a broiler chicken.

160. The method of clause 156 wherein *Campylobacter* inhibition prevents *Campylobacter* disease in the animal.

161. The method of clause 156 wherein the *Campylobacter* inhibition reduces *Campylobacter* disease in the animal.

162. The method of clause 158 wherein the animal is a porcine species and the porcine species is selected from the group consisting of a grow finish pig, a nursery pig, a sow, and a breeding stock pig.

163. The method of any one of clauses 156 to 162 wherein the *Bacillus* strain produces an enzyme selected from the group consisting of an α-galactosidase, a protease, a lipase, an amylase, a xylanase, a cellulase, and combinations thereof.

164. The method of any one of clauses 156 to 163 further comprising the step of administering to the animal another bacterial strain selected from the group consisting of another *Bacillus* strain, a lactic acid bacterial strain, and combinations thereof.

165. The method of any one of clauses 156 to 164 wherein the strain administered is *Bacillus* strain 101 (NRRL No. B-67218).

166. The method of any one of clauses 156 to 164 wherein the strain administered is *Bacillus* strain 235 (NRRL No. B-67219).

167. The method of any one of clauses 156 to 166 wherein the *Bacillus* strain is administered in the feed composition at a dose of about $1.0 \times 10^3$ CFU/gram of the feed composition to about $5.0 \times 10^{12}$ CFU/gram of the feed composition.

168. The method of any one of clauses 156 to 166 wherein the *Bacillus* strain is administered in the feed composition at a dose of about $1.0 \times 10^3$ CFU/gram of the feed composition to about $1.0 \times 10^7$ CFU/gram of the feed composition.

169. The method of any one of clauses 156 to 166 wherein the *Bacillus* strain is administered in the feed composition at a dose greater than about $7.0 \times 10^4$ CFU/gram of the feed composition.

170. The method of any one of clauses 156 to 169 further comprising the step of administering an antibiotic to the animal.

171. The method of any one of clauses 156 to 170 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

172. The method of clause 171 wherein the enzyme is an NSPase or a phytase.

173. The method of clause 158 wherein the animal is a sow and the *Bacillus* strain is administered during lactation.

174. The method of clause 158 wherein the animal is a sow and the *Bacillus* strain is administered during gestation.

175. The method of any one of clauses 156 to 174 wherein the feed composition is administered daily to the animal.

176. The method of clause 158 wherein the animal is selected from the group consisting of a chicken, a pig, a horse, a pony, a cow, a turkey, a goat, a sheep, a quail, a pheasant, an ostrich, a duck, and combinations thereof.

In various embodiments, the animal to which a feed additive, a feed composition, or drinking water as described herein is administered can be selected from the group consisting of a poultry species, a porcine species, a caprine species, a bovine species, an ovine species, an equine species, and a companion animal. In the embodiment where the animal is a companion animal, the companion animal can be, for example, a canine species or a feline species. In the embodiment where the animal is a porcine species, the porcine species can be selected from the group consisting of a grow finish pig, a nursery pig, a sow, and a breeding stock pig. In various exemplary embodiments, the animal can be selected from the group consisting of a chicken (e.g., a broiler or a layer), a pig, a horse, a pony, a cow, a turkey, a goat, a sheep, a quail, a pheasant, an ostrich, a duck, a fish (e.g., a tilapia, a catfish, a flounder, or a salmon), a crustacean (e.g., a shrimp or a crab), and combinations thereof. In another embodiment, the feed additive, feed composition, or drinking water as described herein could be administered to a human.

In another embodiment, *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, can reduce contamination by detrimental bacteria of meat products produced from the animal.

In various embodiments of the method, commercial package, feed additive, feed composition, or additive for drinking water described herein, the *Bacillus* strain can have an effect selected from the group consisting of maintaining microbial balance in the gut of the animal, preventing or reducing *E. coli, Salmonella*, and/or *Campylobacter* disease in the animal, improving animal performance or health, maintaining gut health in the animal, reducing detrimental pathogens in the gut of the animal, odor reduction, reducing detrimental pathogens in the urine or feces of the animal, preserving the growth of beneficial bacteria in the gut of the animal, and preventing or reducing prolapse in the animal.

In any of the embodiments, described herein the *Bacillus* strain can be a *Bacillus subtilis* strain (e.g., strains 86, 300, 101, 235, A12, 681, 721, and 54), or a *Bacillus pumilus* strain (e.g., strains 102 and 177).

In any embodiments described herein, the *Bacillus* strains can be administered alone or in any combination, or can be in the form of any composition described herein so that the strains are alone or in any combination in the compositions described herein. The *Bacillus* strains described herein can also be used in combination with other microbial strains, including other *Bacillus* strains or *Lactobacillus* strains. Exemplary combinations include *Bacillus* strains A12, 54, 681, and 721 (described herein) in any combination with any combination of *Bacillus* strains 86, 300, 101, 102, 177, and 235, described in U.S. Appl. Publication No. U.S. 2017/0079308 and U.S. Appl. Publication No. U.S. 2017/0246224, each incorporated herein by reference. Another exemplary combination includes *Bacillus* strains A12, 54, 681, 721, 101, 235, 86, and 300 in any combination.

In one embodiment, a method of feeding an animal is provided. The method comprises the step of administering to the animal a feed composition or drinking water comprising an effective amount of an additive comprising an isolated *Bacillus* strain selected from the group consisting *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.

In another embodiment, a method of feeding an animal is provided. The method comprises the step of administering to the animal a feed composition or drinking water comprising an effective amount of an additive comprising an isolated *Bacillus* strain selected from the group consisting *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, wherein the *Bacillus* strain causes *E. coli, Salmonella*, and/or *Campylobacter* inhibition in the animal.

In another embodiment, a method of feeding an animal is provided comprising the step of administering to the animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, wherein the *Bacillus* strain causes *Campylobacter* inhibition in the animal.

In one embodiment of the invention, an effective amount of the *Bacillus* strain can be administered to inhibit *E. coli, Salmonella*, and/or *Campylobacter* in the animal. As used herein, "inhibit *E. coli, Salmonella*, and/or *Campylobacter*" can mean reducing *E. coli, Salmonella*, and/or *Campylobacter* disease, preventing *E. coli, Salmonella*, and/or *Campylobacter* disease, maintaining the normal microbial balance in the animal, reducing the number of detrimental *E. coli, Salmonella*, and/or *Campylobacter* in the animal, reducing the activity of *E. coli, Salmonella*, and/or *Campylobacter* in the animal, or reducing the symptoms of *E. coli, Salmonella*, and/or *Campylobacter* disease in the animal, or combinations thereof. By "effective amount" is meant an amount of the *Bacillus* strain (e.g., strain A12, or 54, or 681, or 721, or 101, or 235) capable of *E. coli, Salmonella*, and/or *Campylobacter* inhibition or capable of controlling a detrimental effect of *E. coli, Salmonella*, and/or *Campylobacter*, as described below, by any mechanism.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain prevents or reduces prolapse in the animal.

In still another embodiment, a method of controlling a detrimental effect of *E. coli* and/or *Campylobacter* is provided. The method comprises the steps of administering to an animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, and controlling the detrimental effect of *E. coli* and/or *Campylobacter* in the animal wherein the detrimental effect is prolapse in the animal.

For methods involving reducing or preventing prolapse in the animal, "reducing," "reduces," "reduce", "preventing," "prevents," or "prevent" can mean reducing prolapse, preventing prolapse, or reducing the symptoms of prolapse in the animal, or combinations thereof. For methods involving reducing or preventing prolapse in the animal an "effective amount" of the *Bacillus* strain means an amount capable of reducing or preventing prolapse, by any mechanism. In other embodiments, an "effective amount" of the *Bacillus* strain means an amount capable of controlling a detrimental effect of *E. coli* and/or *Campylobacter*, by any mechanism, wherein the detrimental effect is prolapse. In these embodiments, the prolapse that can be reduced or prevented or controlled includes vaginal and/or uterine prolapse and rectal and/or anal prolapse. In these embodiments, vaginal and/or uterine prolapse can be referred to as pelvic organ prolapse.

In embodiments described herein wherein the compositions of the present invention comprising *Bacillus* strains A12, and/or 54, and/or 681, and/or 721, and/or 300, and/or 101, and/or 235, and/or 86, and/or 102, and/or 177, or strains having their identifying characteristics, are administered to an animal, the compositions are preferably administered to animals orally in a feed composition or in drinking water, but any other effective method of administration known to those skilled in the art may be utilized such as in a paste, a liquid drench, a top dress, or a capsule. In one illustrative embodiment, the *Bacillus* strains A12, and/or 54, and/or 681, and/or 721, and/or 300, and/or 101, and/or 235, and/or 86, and/or 102, and/or 177, or strains having their identifying characteristics, are provided in the form of an additive for addition to the drinking water of an animal. In another embodiment, the strains may be used as a litter treatment.

In another illustrative embodiment, the *Bacillus* strains A12, and/or 54, and/or 681, and/or 721, and/or 300, and/or 101, and/or 235, and/or 86, and/or 102, and/or 177, or strains having their identifying characteristics, are provided in the form of a feed additive for addition to a feed composition. The feed composition may contain *Bacillus* strain A12, and/or 54, and/or 681, and/or 721, and/or 300, and/or 101, and/or 235, and/or 86, and/or 102, and/or 177, or strains having their identifying characteristics, in a mixture with an animal feed blend, including any art-recognized animal feed blend or any animal feed blend described herein. As used herein, "feed composition" or "animal feed composition" means a feed composition comprising *Bacillus* strain A12, and/or *Bacillus* strain 54, and/or *Bacillus* strain 682, and/or *Bacillus* strain 721, and/or 300, and/or 101, and/or 235, and/or 86, and/or 102, and/or 177, or strains having their identifying characteristics, in a mixture with an animal feed blend, and, optionally any other components that could be used in a feed composition, including other bacterial strains, such as other *Bacillus* strains or *Lactobacillus* strains. In one embodiment, the feed composition may be in the form of a ground meal.

Any animal feed blend, including those known in the art and those described herein, may be used in accordance with the methods and compositions described in this patent application, such as rapeseed meal, cottonseed meal, soybean meal, cornmeal, barley, wheat, silage, and haylage. In various embodiments, the animal feed blend can be supplemented with *Bacillus* strain A12, and/or *Bacillus* strain 54, and/or *Bacillus* strain 681, and/or *Bacillus* strain 721, and/or 300, and/or 101, and/or 235, and/or 86, and/or 102, and/or 177, or strains having their identifying characteristics, but other ingredients may optionally be added to the animal feed blend, including other bacterial strains, such as other *Bacillus* strains or *Lactobacillus* strains.

In various illustrative embodiments, optional ingredients of the animal feed blend include sugars and complex carbohydrates such as both water-soluble and water-insoluble monosaccharides, disaccharides, and polysaccharides. Other optional ingredients include dried distillers grain solubles, fat (e.g., crude fat), phosphorous, sodium bicarbonate, limestone, salt, phytate, calcium, sodium, sulfur, magnesium, potassium, copper, iron, manganese, zinc, ash, fish oil, an oil derived from fish meal, raw seed (e.g., flaxseed), an antioxidant, and starch. In another embodiment, minerals may be added in the form of a mineral premix.

Optional amino acid ingredients that may be added to the animal feed blend are arginine, histidine, isoleucine, leucine, lysine, cysteine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. In another embodiment, vitamins may be added in the form of a vitamin premix. In yet another embodiment, protein ingredients may be added to the animal feed blend and include protein obtained from meat meal, bone meal, or fish meal, liquid or powdered egg, fish solubles, crude protein, and the like.

In another illustrative aspect, any medicament ingredients known in the art may be added to the animal feed blend or to an additive for the drinking water of the animal, such as antibiotics. In various embodiments, the antibiotic is selected from the group consisting of ampicillin, chloramphenicol, ciprofloxacin, clindamycin, tetracycline, chlortetracycline, Denagard™ (i.e., tiamulin), BMD™ (i.e., bacitracin methylene disalicylate), Carbadox™ (i.e., carbadox), Stafac™ (i.e., virginiamycin), erythromycin, levofloxacin, trimethoprim/sulfamethoxazole, trimethoprim, daptomycin, rifampicin, Tylan™ (i.e., tylosin), Pulmotil™ (i.e., tilmicosin), vancomycin, and combinations thereof. In another embodiment, the animal feed blend, the feed composition, the feed additive, or the additive for the drinking water of the animal may contain no antibiotics.

In another illustrative embodiment, one or more enzymes may be added to the animal feed blend. In various embodiments, the enzymes that may be added include a galactosidase, a phytase, a protease, a lipase, an amylase, a hemicellulase, an arabinoxylanase, a xylanase, a cellulase, an NSPase, combinations thereof, and any other enzyme that improves the effectiveness of the feed composition for *E. coli*, *Campylobacter*, or *Salmonella* inhibition or controlling a detrimental effect of *E. coli*, *Campylobacter*, or *Salmonella*, or preventing or reducing prolapse in the animal, or controlling detrimental effects of prolapse in the animal. In yet another embodiment, yeast, fungi (e.g., *Aspergillus* or *Trichoderma*), or micronutrients may be added to the animal feed. Any of the ingredients described above that are suitable for addition to an additive for the drinking water of the animal may be added as a component of the additive for the drinking water of the animal as described herein.

In various illustrative embodiments, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics), or any other bacterial strains added in addition to *Bacillus* strain A12, and/or 54, and/or 681, and/or 721, and/or 300, and/or 101, and/or 235, and/or 86, and/or 102, and/or 177, or strains having their identifying characteristics, can be administered in the feed composition at a dose of about $1.0 \times 10^3$ CFU/gram of the feed composition to about $5.0 \times 10^{12}$ CFU/gram of the feed composition or at a dose of about $1.0 \times 10^3$ CFU/gram of the feed composition to about $1.0 \times 10^7$ CFU/gram of the feed composition. In other embodiments, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics) is administered in the feed composition at a dose greater than about $1.0 \times 10^3$ CFU/gram of the feed composition, at a dose greater than about $1.1 \times 10^3$ CFU/gram of the feed composition, at a dose greater than about $1.25 \times 10^3$ CFU/gram of the feed composition, at a dose greater than about $1.5 \times 10^3$ CFU/gram of the feed composition, at a dose greater than about $1.75 \times 10^3$ CFU/gram of the feed composition, at a dose greater than about $1.0 \times 10^4$ CFU/gram of the feed composition, at a dose greater than about $2.0 \times 10^4$ CFU/gram of the feed composition, at a dose greater than about $3.0 \times 10^4$ CFU/gram of the feed composition, at a dose greater than about $4.0 \times 10^4$ CFU/gram of the feed composition, at a dose greater than about $5.0 \times 10^4$ CFU/gram of the feed composition, at a dose greater than about $6.0 \times 10^4$ CFU/gram of the feed composition, at a dose greater than about $7.0 \times 10^4$ CFU/gram of the feed composition, at a dose greater than about $8.0 \times 10^4$ CFU/gram of the feed composition, at a dose greater than about $1.0 \times 10^5$ CFU/gram of the feed composition, at a dose greater than about $1.0 \times 10^6$ CFU/gram of the feed composition, at a dose greater than about $1.0 \times 10^7$ CFU/gram of the feed composition, at a dose greater than about $1.0 \times 10^8$ CFU/gram of the feed composition, at a dose greater than about $1.0 \times 10^9$ CFU/gram of the feed composition, at a dose greater than about $1.0 \times 10^{10}$ CFU/gram of the feed composition, at a dose greater than about $1.0 \times 10^{11}$ CFU/gram of the feed composition, or at a dose greater than about $1.0 \times 10^{12}$ CFU/gram of the feed composition. In yet another embodiment, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics) is administered in the feed composition at a dose of about $7.3 \times 10^4$ CFU/gram of the feed composition. In another embodiment, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics), or any other bacterial strains added in addition to *Bacillus* strain A12, and/or 54, and/or 681, and/or 721, and/or 300, and/or 101, and/or 235, and/or 86, and/or 102, and/or 177, or strains having their identifying characteristics, can be administered in the feed composition at a dose of about $1.0 \times 10^2$ CFU/gram of the feed composition to about $5.0 \times 10^{12}$ CFU/gram of the feed composition or at a dose of about $1.0 \times 10^2$ CFU/gram of the feed composition to about $1.0 \times 10^7$ CFU/gram of the feed composition, or at a dose greater than about $1.0 \times 10^2$ CFU/gram of the feed composition. In another embodiment, any of the dosages described herein can be in CFU/ml of drinking water in embodiments where the strains are administered in the drinking water of the animal.

In various embodiments, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics) for use in accordance with the methods and compositions described herein can be selected from the group consisting of *Bacillus* strain A12 (NRRL No. B67516), 54 (NRRL No. B67517), 681 (NRRL No. B67515), 721 (NRRL No. B67514), 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof. *Bacillus* strains A12, 54, 681, and 721 were deposited on Sep. 14, 2017 at the Agricultural Research Service Culture Collection (NRRL), National Center for Agricultural Utilization Research, Agricultural Research Service, USDA, 1815 North University Street, Peoria, Illinois 61604-3999, and were given accession numbers B67516, B67517, B67515, and B67514, respectively. The deposits were made under the provisions of the Budapest Treaty on the International Recognition of the Deposit of Microorganisms for the Purposes of Patent Procedure. The NRRL strain designations are B67516, B67517, B67515, and B67514 which are equivalent to *Bacillus* strain A12, 54, 681, and 721, respectively, as referred to in the application. *Bacillus* strain MDG86 and *Bacillus* strain MDG300 were deposited on Mar. 14, 2014 at the Agricultural Research Service Culture Collection (NRRL), National Center for Agricultural Utilization Research, Agricultural Research Service, USDA, 1815 North University Street, Peoria, Illinois 61604-3999, and were given accession numbers B-50944 and B-50943, respectively. The deposits were made under the provisions of the Budapest Treaty on the International Recognition of the Deposit of Microorganisms for the Purposes of Patent Procedure. The NRRL strain designations are MDG86 and MDG300, which are equivalent to *Bacillus* strain 86 and 300, respectively, as referred to in the application. *Bacillus* strain MDG 101 and *Bacillus* strain MDG 235 were deposited on Jan. 4, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67218 and B-67219, respectively. *Bacillus* strain MGL177 and *Bacillus* strain MGL102 were deposited on Jun. 7, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67275 and B-67276, respectively. The deposits were made under the provisions of the Budapest Treaty on the International Recognition of the Deposit of Microorganisms for the Purposes of Patent Procedure. The NRRL strain designations are MDG 101, MDG 235, MGL177, and MGL102 which are equivalent to *Bacillus* strain 101, 235, 77, 177, and 102 respectively, as referred to in the application.

Any of these strains can be administered alone or in combination in the form of a feed composition (e.g., a complete feed comprising an animal feed blend) or drinking water for an animal. In one embodiment, multiple strains are administered in combination in a single composition. In another embodiment, multiple strains are administered in combination in separate compositions. In one illustrative embodiment, any of these strains is isolated from a high performing grow finish pig.

In another embodiment, one or more of the *Bacillus* strains described in the preceding paragraphs (e.g., *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains having their identifying characteristics) can be administered to the animal along with another bacterial strain selected from the group consisting of another *Bacillus* strain, a lactic acid bacterial strain, and combinations thereof. In yet another embodiment, one or more of the *Bacillus* strains described in the preceding paragraphs (e.g., *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains having their identifying characteristics) can be administered to the animal along with any other bacterial strain effective to inhibit or control detrimental effects of *E. coli, Salmonella*, and/or *Campylobacter* in the animal, or prevent or reduce prolapse or control detrimental effects of *E. coli* or *Campylobacter* to control prolapse in the animal.

As used herein "a strain having all of the identifying characteristics of" *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177 can be a mutant strain having all of the identifying characteristics of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177 (e.g., a DNA fingerprint based on DNA analysis that corresponds to the DNA fingerprint of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, enzyme activities that correspond to *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, antimicrobial activity that corresponds to *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, antibiotic sensitivity and tolerance profiles that correspond to *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or combinations of these identifying characteristics). In alternate embodiments, the mutation can be a natural mutation, or a genetically engineered mutation. In another embodiment, "a strain having all of the identifying characteristics of" *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, can be a strain, for example, produced by isolating one or more plasmids from *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, and introducing the one or more plasmids into another bacterium, such as another *Bacillus* strain, as long as the one or more plasmids contain DNA that provides the identifying characteristics of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177 (e.g., a DNA fingerprint based on DNA analysis that corresponds to the DNA fingerprint of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177).

The feed composition or drinking water comprising *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, may be administered to the animal for any time period that is effective to inhibit *E. coli, Salmonella*, and/or *Campylobacter* or control a detrimental effect of *E. coli, Salmonella*, and/or *Campylobacter*, or reduce or prevent prolapse or control a detrimental effect of *E. coli* or *Campylobacter* to control prolapse in the animal, or combinations thereof. For example, in one embodiment the feed composition or drinking water may be provided to the animal daily. In an alternate embodiment, the feed composition or drinking water may be administered to the animal during lactation and/or during gestation. The time periods for administration of the feed composition or drinking water described above are non-limiting examples and it should be appreciated that any time period or administration schedule determined to be effective to inhibit *E. coli, Salmonella*, and/or *Campylobacter* or control a detrimental effect of *E. coli, Salmonella*, and/or *Campylobacter*, or reduce or prevent prolapse or control a detrimental effect of *E. coli* or *Campylobacter* to control prolapse in the animal, or combinations thereof, may be used.

As described herein, one of the method embodiments is a method of feeding an animal by administering to the animal a feed composition or drinking water comprising an effective amount of an additive comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof, wherein the *Bacillus* strain controls a detrimental effect of *E. coli, Salmonella,* and/or *Campylobacter*. Any of the applicable above-described embodiments can apply to this embodiment.

In yet another method embodiment, a method of controlling a detrimental effect of *Campylobacter* is provided. The method comprises the steps of administering to an animal a feed composition or drinking water comprising an effective amount of an additive comprising an isolated *Bacillus* strain selected from the group consisting of *Bacillus* strain 101 (NRRL No. B-67218), 235 (NRRL No. B-67219), a strain having all of the identifying characteristics of *Bacillus* strain 101 (NRRL No. B-67218), a strain having all of the identifying characteristics of *Bacillus* strain 235 (NRRL No. B-67219), and combinations thereof, and controlling the detrimental effect of *Campylobacter* in the animal. Any of the applicable above-described embodiments can apply to this embodiment.

In these embodiments, "controlling a detrimental effect of *E. coli, Salmonella,* and/or *Campylobacter*" can mean reducing *E. coli, Salmonella,* and/or *Campylobacter* disease, preventing *E. coli, Salmonella,* and/or *Campylobacter* disease, maintaining the normal microbial balance in the animal, reducing the number of detrimental *E. coli, Salmonella,* and/or *Campylobacter* in the animal, reducing the activity of *E. coli, Salmonella,* and/or *Campylobacter* in the animal, or reducing the symptoms of *E. coli, Salmonella,* and/or *Campylobacter* disease in the animal, or combinations thereof. By "effective amount" is meant an amount of the *Bacillus* strain (e.g., *Bacillus* strain A12, and/or *Bacillus* strain 54, and/or *Bacillus* strain 681, and/or *Bacillus* strain 721) capable of controlling a detrimental effect of *E. coli, Salmonella,* and/or *Campylobacter*, as described above, by any mechanism.

In additional embodiments of the invention, compositions comprising *Bacillus* strain A12, and/or *Bacillus* strain 54, and/or *Bacillus* strain 681, and/or *Bacillus* strain 721 are provided. In one embodiment, a commercial package is provided comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.

In another embodiment, a feed additive for an animal feed is provided comprising an isolated *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.

In yet another embodiment, an additive for the drinking water of an animal is provided comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.

In yet another illustrative aspect of the invention, an animal feed composition is provided comprising an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof.

In any of these composition embodiments, *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, can be added to the compositions to reduce or prevent prolapse in the animal, or to control a detrimental effect of or to inhibit *E. coli* or *Campylobacter* or *Salmonella*. In one embodiment, the control or inhibition of *Campylobacter* is to control prolapse in the animal.

In another embodiment an isolated *Bacillus* strain selected from the group consisting of *Bacillus* strain A12 (NRRL No. B67516), 54 (NRRL No. B67517), 681 (NRRL No. B67515), and 721 (NRRL No. B67514), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), and combinations thereof can be used in reducing detrimental bacterial contaminants in meat produced from the animal.

In one embodiment, the feed additive for addition to an animal feed blend to produce a complete feed composition can be mixed with the animal feed blend, for example, with an automated micro-nutrient delivery system, or, for example, by hand-weighing and addition to achieve any of the doses of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, described herein, for administration to the animal in the form of a complete feed composition. The mixing can also be done by any other suitable method known in the art for combining direct-fed microbials with an animal feed blend to obtain a uniform mixture. In various embodiments, the mixing can be done for any suitable time period (e.g., about 1 to about 4 minutes). In the embodiment where *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, is in the form of an additive for the drinking water of the animal, the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, can be in the form of, for example, a powder, a liquid, or pellets, and can be mixed with the drinking water using any suitable method known in the art to achieve any of the doses of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, described herein, for administration to the animal in the drinking water of the animal. *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, can also be fed directly to the animal orally (i.e., by oral insertion) in the form of a powder, a liquid, or a pellet.

In any of the composition embodiments described herein, the *Bacillus* strain *Bacillus* strain A12, and/or *Bacillus* strain 54, and/or *Bacillus* strain 681, and/or *Bacillus* strain 721 can cause an effect selected from the group consisting of inhibiting *E. coli, Salmonella*, and/or *Campylobacter* or controlling a detrimental effect of *E. coli, Salmonella*, and/or *Campylobacter* in the animal. These effects are non-limiting examples of the types of effects *Bacillus* strain *Bacillus* strain A12, and/or *Bacillus* strain 54, and/or *Bacillus* strain 681, and/or *Bacillus* strain 721 can cause. For example, in various embodiments of the method, commercial package, feed additive, feed composition, or additive for drinking water described herein, the *Bacillus* strain can have an effect selected from the group consisting of maintaining microbial balance in the gut of the animal, preventing or reducing *E. coli, Salmonella*, and/or *Campylobacter* disease in the animal, improving animal performance or health, maintaining gut health in the animal, reducing detrimental pathogens in the gut of the animal, odor reduction, reducing detrimental pathogens in the urine or feces of the animal, reducing contamination by detrimental bacteria of meat products produced from the animal, and preserving the growth of beneficial bacteria in the gut of the animal.

In other composition embodiments, the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, can reduce or prevent prolapse in the animal, or control a detrimental effect of *E. coli* or *Campylobacter* to control prolapse in the animal. In these embodiments, the prolapse that can be reduced or prevented or controlled includes vaginal and/or uterine prolapse and rectal and/or anal prolapse.

In one illustrative aspect, the feed additive, additive for the drinking water of the animal, or the feed composition can be in the form of a commercial package. In another illustrative embodiment, the feed additive or additive for the drinking water of the animal, or the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, in the commercial package can be in the form of a concentrate (e.g., about $1 \times 10^8$ to about $5 \times 10^9$ CFU/g) or a superconcentrate (e.g., about $1 \times 10^{10}$ to about $5 \times 10^{12}$ CFU/g). In another embodiment, the feed additive, feed composition, or additive for the drinking water of the animal, or the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, in a composition in a commercial package, can be in a dry form (e.g., a powder), a pelleted form, a liquid form, in the form of a top-dressing, or in the form of a gel, or any other suitable form.

In yet another embodiment, the strains in the form of a commercial package can be, for example, in a dry form (e.g., a powder or freeze-dried form), in a pelleted form, or in a liquid form.

In another illustrative embodiment, the commercial package, feed additive, additive for the drinking water of the animal, or feed composition can further comprise a carrier for the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics. The carrier can be selected from the group consisting of a bran, rice hulls, a salt, mineral oil, a dextrin (e.g., maltodextrin), whey, sugar, sucrose, limestone, yeast culture, dried starch, sodium silico aluminate, silicon dioxide, polypropylene glycol, polysorbate 80, vegetable oil, and combinations thereof. In another embodiment, the carrier can be any suitable carrier known in the art for a direct-fed microbial. In another embodiment, the commercial package, feed additive, additive for the drinking water of the animal, or feed composition can further comprise a binder such as clay, yeast cell wall components, aluminum silicate, glucan, or other known binders. In another embodiment, the commercial package, feed additive, additive for the drinking water of the animal, or feed composition can further comprise inorganic/organic binders, essential oils, and/or organic acids.

In yet other embodiments, the commercial package, feed additive, additive for the drinking water of the animal, or feed composition comprising *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics is in a container for commercial use. In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container for the commercial package, feed additive, additive for the drinking water of the animal, or feed composition comprising *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or

*Bacillus* strain 235, and/or *Bacillus* strain 86, and/or *Bacillus* strain 102, and/or *Bacillus* strain 177, or strains with their identifying characteristics, can comprise plastic, metal, foil, paper, fiber, or cardboard (e.g., a plastic pail, a paper bag, a foil bag, a fiber drum, etc.). The commercial package, feed additive, additive for the drinking water of the animal, or feed composition can further comprise instructions for use of one or more of the *Bacillus* strains.

The following examples are for illustrative purposes only. The examples are non-limiting, and are not intended to limit the invention in any way.

Example 1

In Vitro Studies of Efficacy of 681 and 721 Whole Cell Preparations Against Animal Pathogens Strain specific efficacy was tested using agar cross-streak antimicrobial susceptibility methods known in the art and described below. Briefly, Bs681 and Bs721 were inoculated from frozen glycerol stocks in a single 1 cm wide horizontal streak down the center of a BHI+ agar plate. *Bacillus* streaked plates were incubated aerobically for 16 hours at 37° C., or until a confluent streak of growth was present. FIG. 1A shows antimicrobial screening utilizing the agar cross streak method against various isolates of *Salmonella*. FIG. 1B shows antimicrobial screening utilizing the agar cross streak method against various isolates of *Campylobacter*. FIG. 1C shows antimicrobial screening utilizing the agar cross streak against various isolates of *Escherichia coli*.

Example 2

In Vitro Studies of Efficacy of A12 and 54 Whole Cell Preparations Against Animal Pathogens Using the same techniques as described in the EXAMPLE 1, FIG. 2A, 48 *E. coli* from 11 different farms tested against A12 and 54. FIG. 2B shows data acquired from A12 and 54 strains against 48 susceptible *E. coli* isolates. FIG. 2C shows data acquired from A12 and 54 strains against 3 resistant *Salmonella* isolates.

Example 3

Strain Identification and Uniqueness

Figure 3B:
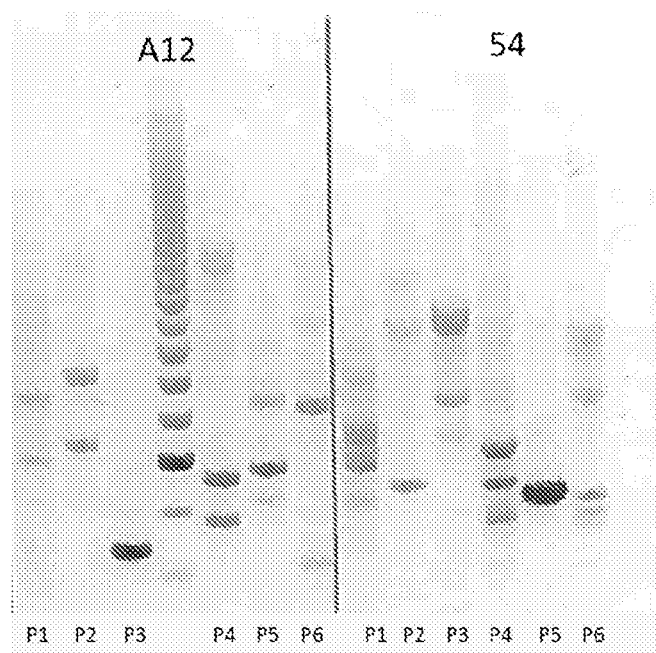
FIG. 3B shows the RAPD testing results for the A12 and 54 strains. All strains were novel and unique from one another.

The Randomly Amplified Polymorphic DNA PCR method (hereafter referred to as RAPD-PCR) was used to identify genetic variability of each strain. Preparation of the DNA to be used in the RAPD-PCR reaction was done by using the QIAGEN® Tissue and Blood single column kit (QIAGEN®, Venlo, The Netherlands). To obtain DNA, an overnight culture was prepared, struck for purity, pelleted, and DNA was extracted following the manufacturer's protocol. RAPD The RAPD-PCR reaction was performed with the following run conditions in a thermal cycler: 95° C. 5 min, followed by 45 cycles of (95° C. 1 min, 36° C. 1 min, 72° C. 2 min), followed by 72° C. 7 min, and finished with a 4° C. indefinite hold to preserve the product. The RAPD-PCR product was analyzed by gel electrophoresis. FIG. 3A illustrates RAPD-PCR results for 681 and 721, with the first lane being a molecular weight ladder and each subset of lanes representing the six different primer sets used, and within each subset, lane A represents a proprietary strain, lane B represents strain 681, and lane C represents strain 721. FIG. 3B illustrates RAPD-PCR results for A12 and 54, with each subset of lanes representing the two strains, A12 and 54, and within each subset, lane P1-P6 representing the six different primer sets used and a molecular ladder.

Example 4

Microbial Pathogen Genes and *Campylobacter* Inhibition Associated with Prolapse Events In order to help determine what microbial pathogen genes might be prompting prolapse events in a particular swine herd, one baseline and three follow up samplings centered around prolapse events were obtained from both affected and non-affected animals. The time between baseline samples and prolapse event samples was approximately eight weeks. Prolapsed animals were sacrificed along with their healthy cohorts and the descending colon was swabbed to maintain sampling consistency. Attempts were made to determine if unique pathogens or profiles of pathogens were present in animals that had recently prolapsed. RT-PCR and statistical analysis were utilized to identify particular enteric pathogen genes known to contribute to GI symptomology in swine.

All *Campylobacter* strains were obtained from swine rectal swabs and were cultured for 48 hours at 42° C. on C2-esterase specific *Campylobacter* media (RF labs) under microaerophilic conditions. These isolates were subsequently grown in brain heart infusion broth at 42° C. in microaerophilic conditions in preparation for the cross streak assay. *Bacillus* strains 300, 101, 235, 86, A12, 102, 681, 721, 54 and 177 were obtained from glycerol stocks.

Strain specific efficacy was tested using agar cross-streak antimicrobial susceptibility methods known in the art and described herein. Briefly, the 10 aforementioned *Bacillus* strains were inoculated from frozen glycerol stocks in a single 1 cm wide horizontal streak down the center of a BHI+ agar plate. *Bacillus* streaked plates were incubated aerobically for 16 hours at 37° C., or until a confluent streak of growth was present. *Campylobacter* strains were then struck perpendicularly to the original *Bacillus* streak (up to 1 mm), taking care not to touch the already growing *Bacillus*. These plates containing both the pre-grown *Bacillus* and the newly struck *Campylobacter* were incubated at 42° C. for 24 hours under microaerophilic conditions and the zone of inhibition was recorded.

Figure 4A:
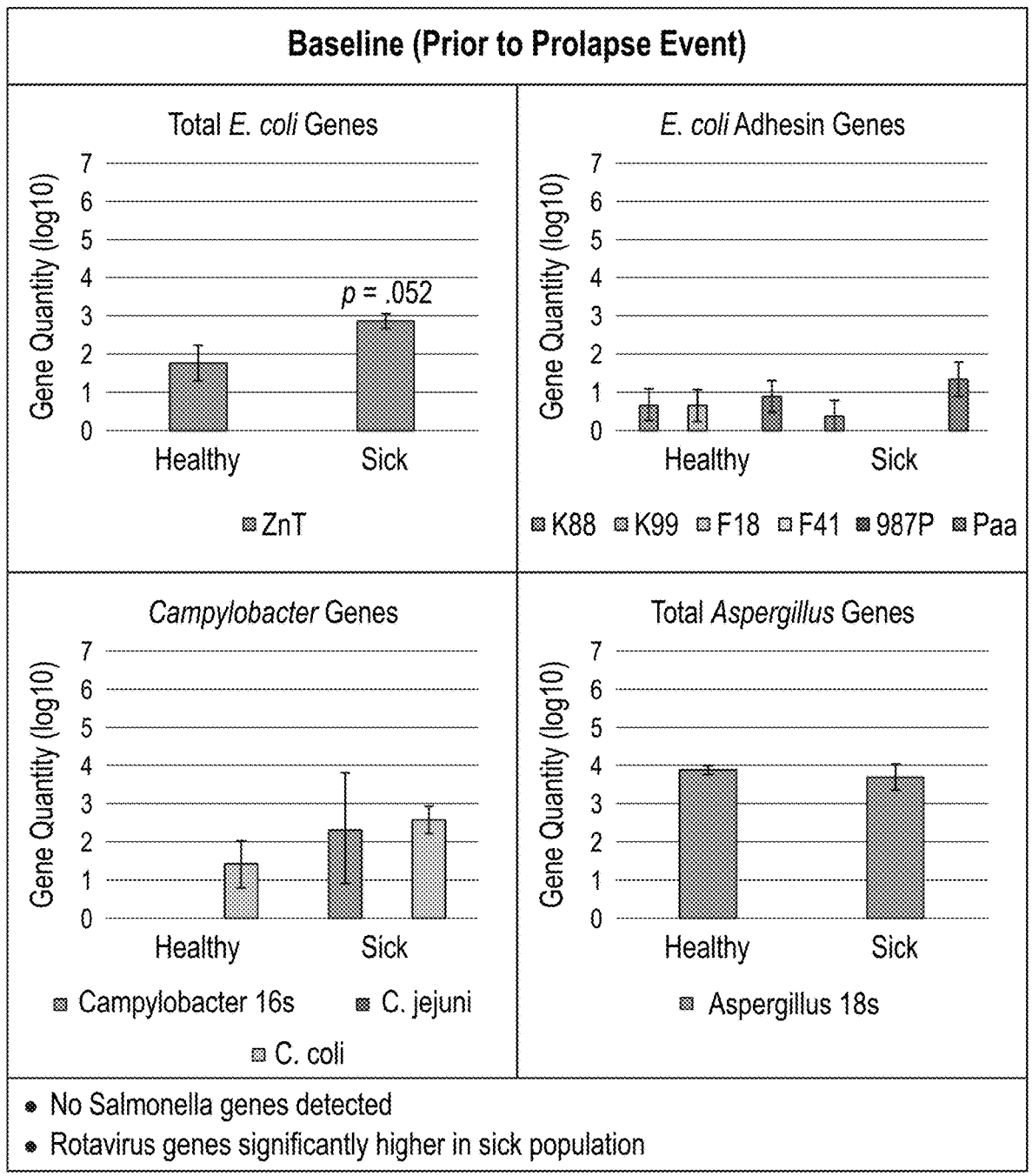
FIG. 4A shows virulence gene quantitation of various pathogens identified from samples taken during the baseline.
Figure 4A:
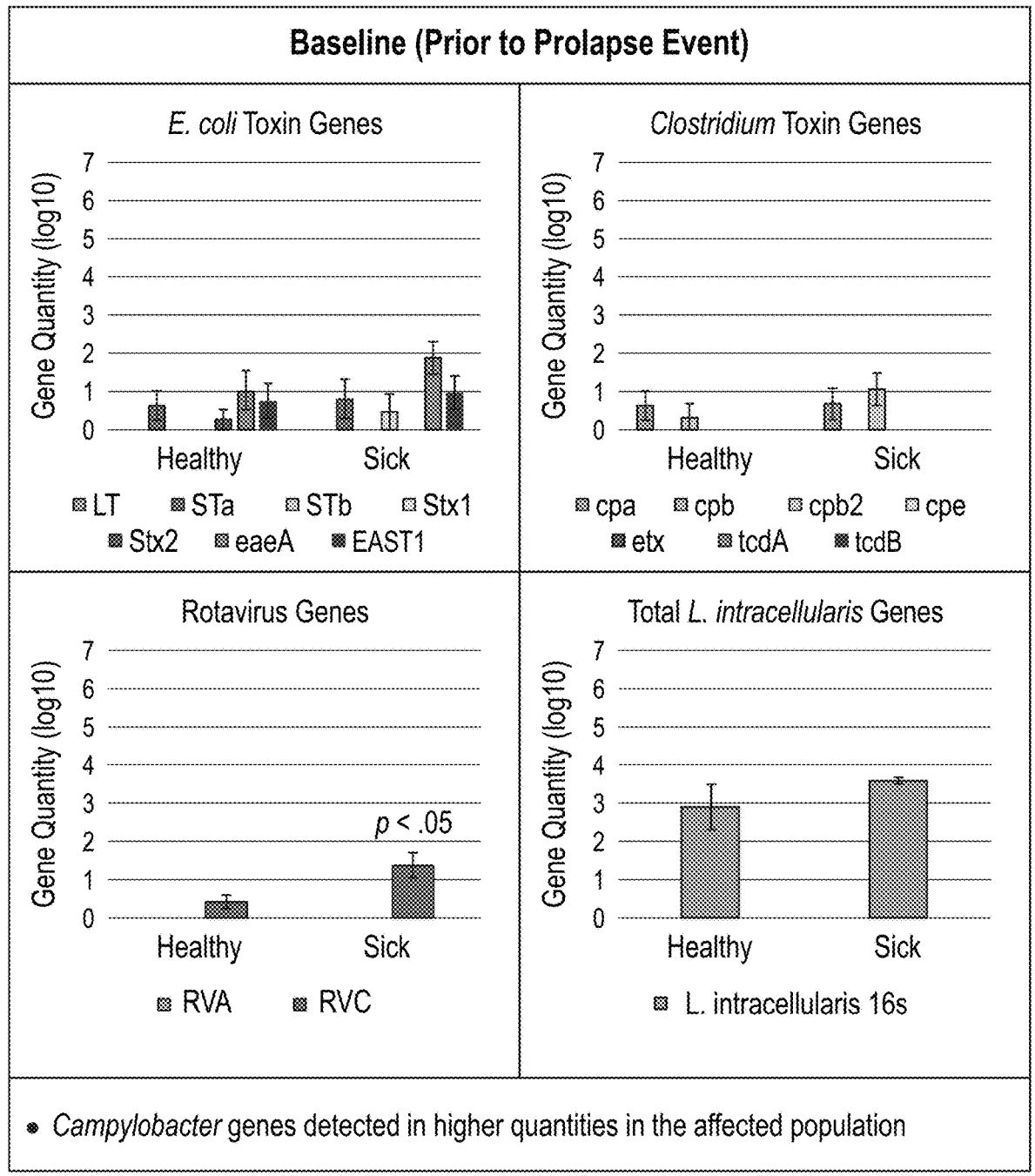
Figure 4B:
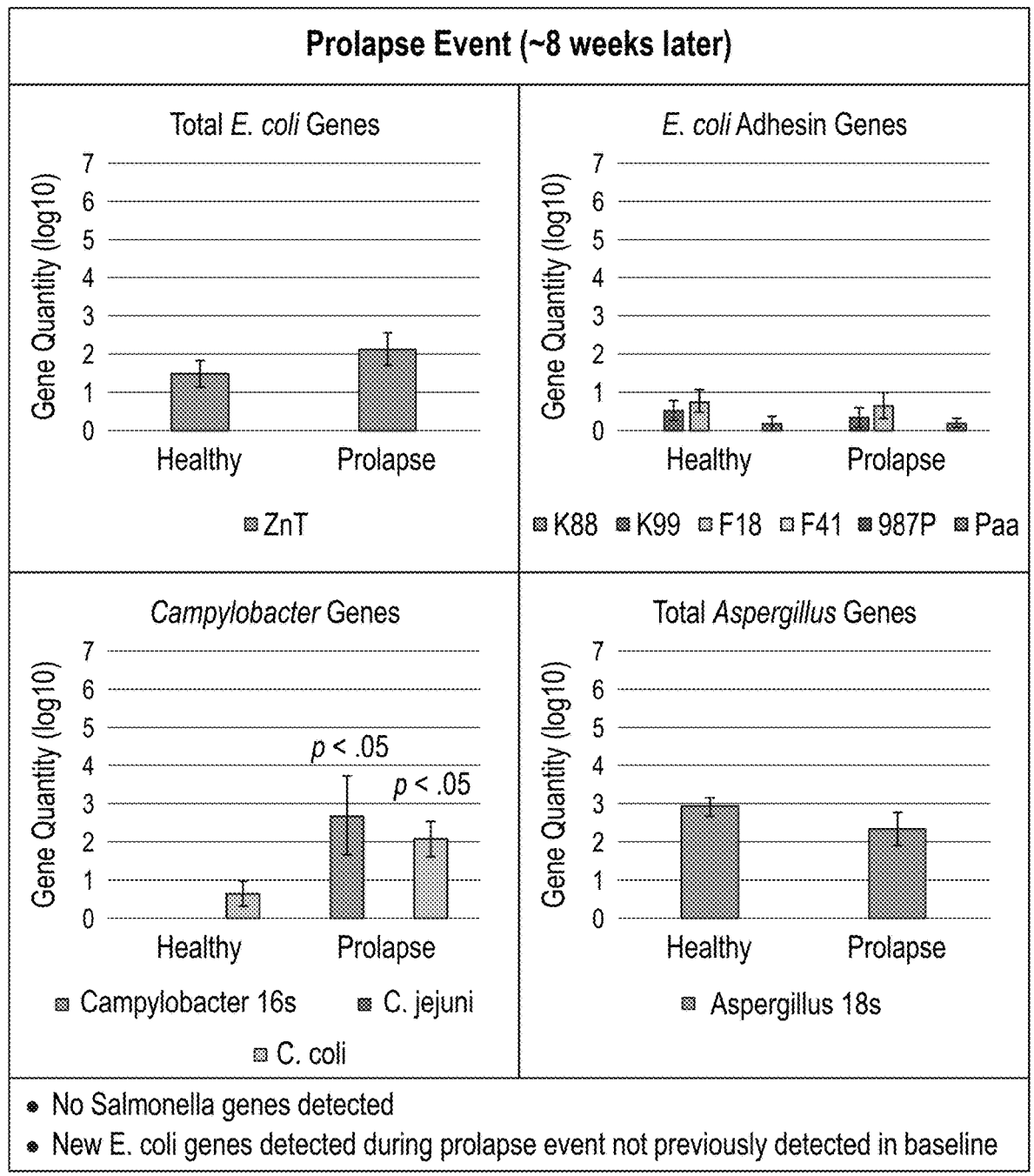
FIG. 4B shows virulence gene quantitation of various pathogens identified from samples taken during the prolapse event.
Figure 4B:
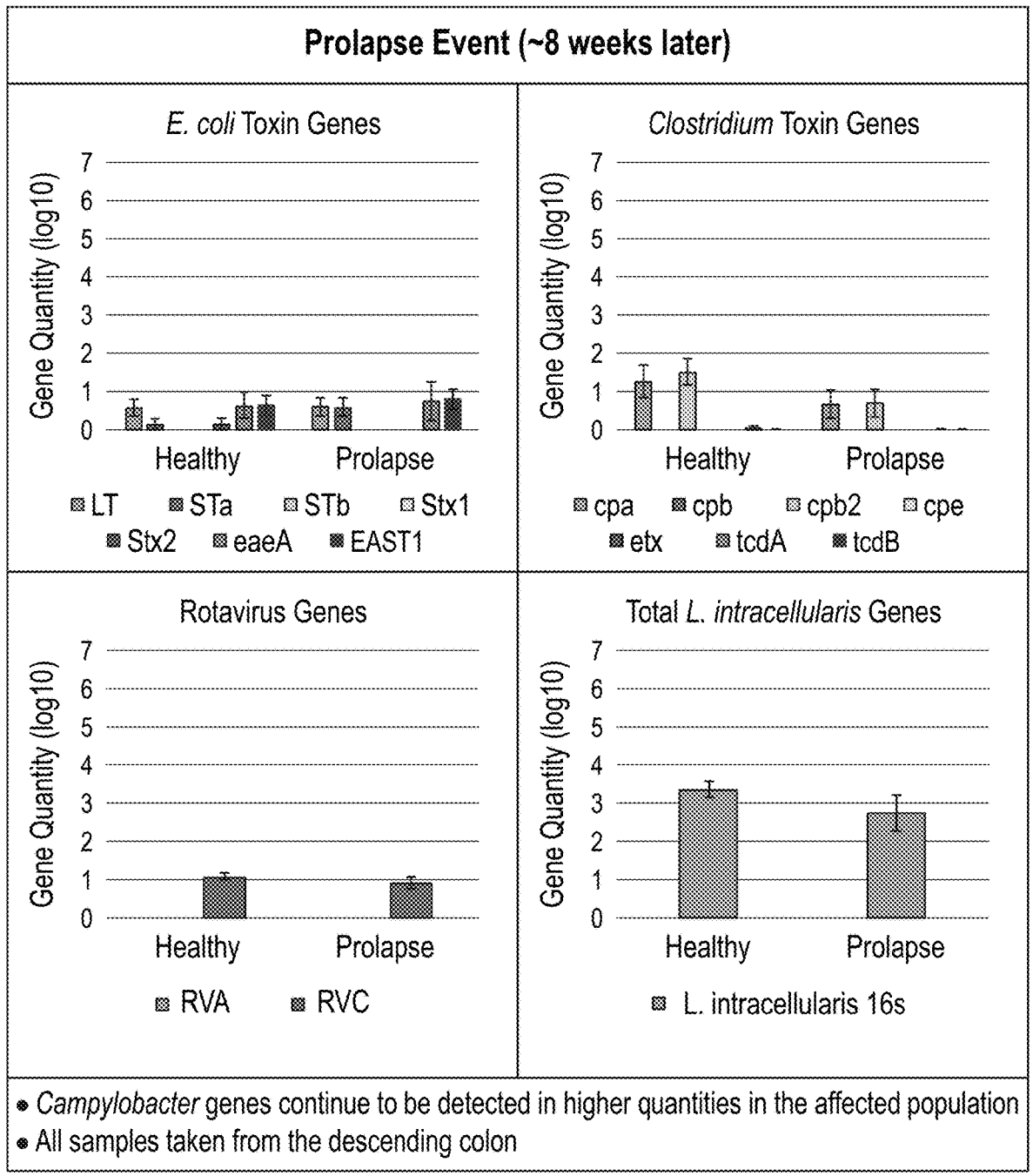
Figure 6:
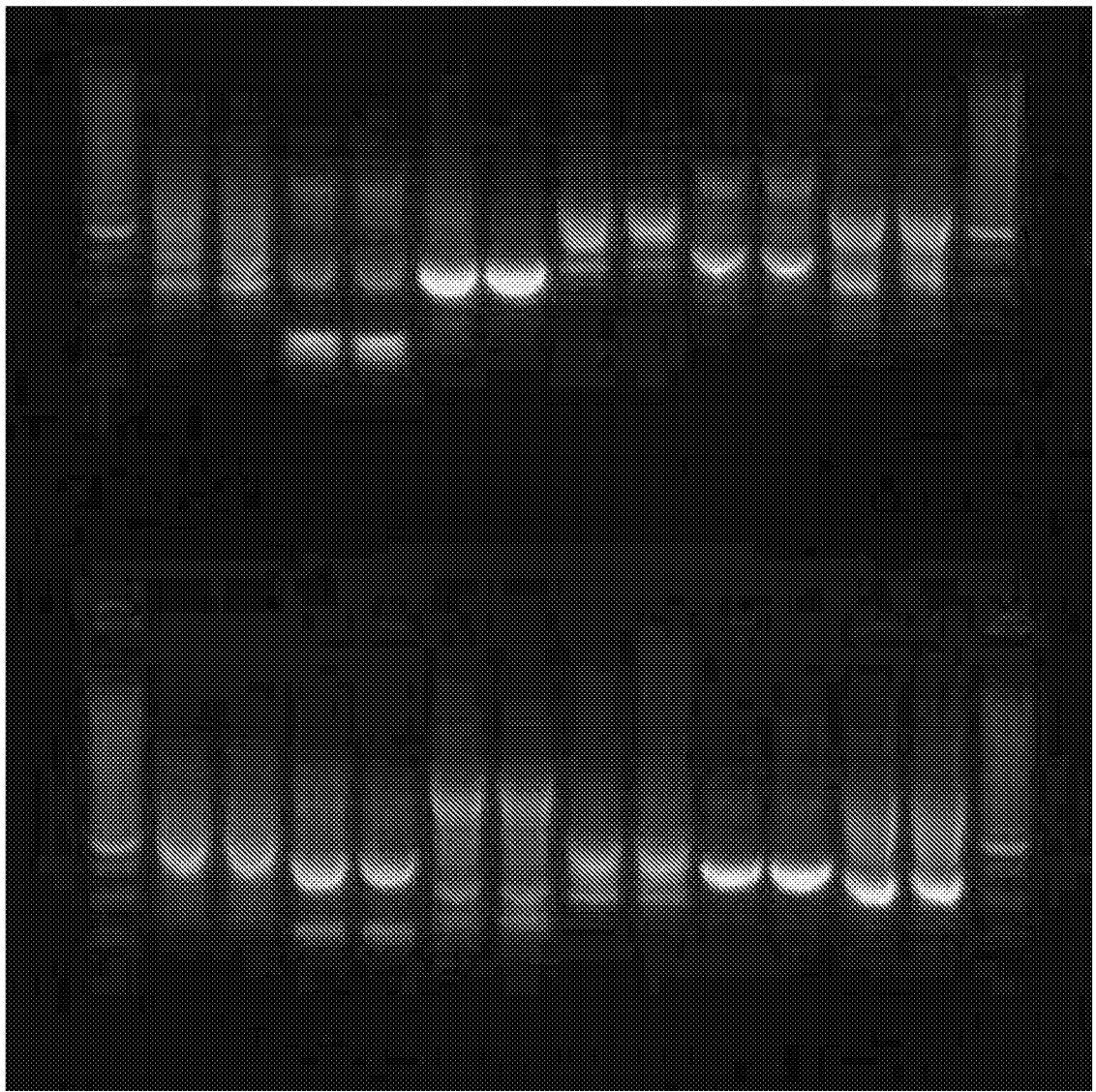
FIG. 6 shows a photograph of a gel displaying RAPD PCR profiles (Primer 1 to 6) for *Bacillus* strains 86 and 300. Strain 86 has the top profile and strain 300 has the bottom profile. The leftmost and rightmost lanes have markers and each set of two consecutive lanes between the markers corresponds to Primers 1 to 6 going from left to right.
Figure 7:
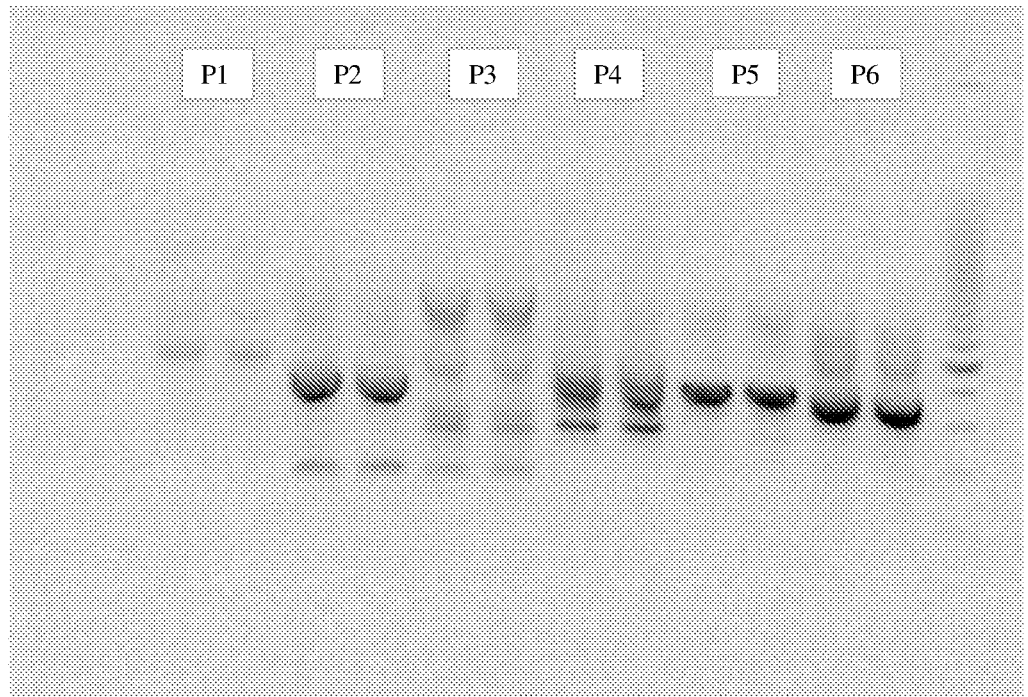
FIG. 7 shows a photograph of a gel displaying a RAPD PCR profile (Primer 1 to 6) for *Bacillus* strain 101. For Primer 1, faint bands appear at approximately 1000, 1500, and greater than 1600 base pairs. For Primer 2, an intense band appears at 650 base pairs and a faint band appears at approximately 400 base pairs. For Primer 3, a faint band appears at approximately 400 base pairs, a faint double band appears at 600 and 700 base pairs, and faint bands appear at 1000 and 1400 base pairs.
Figure 8:
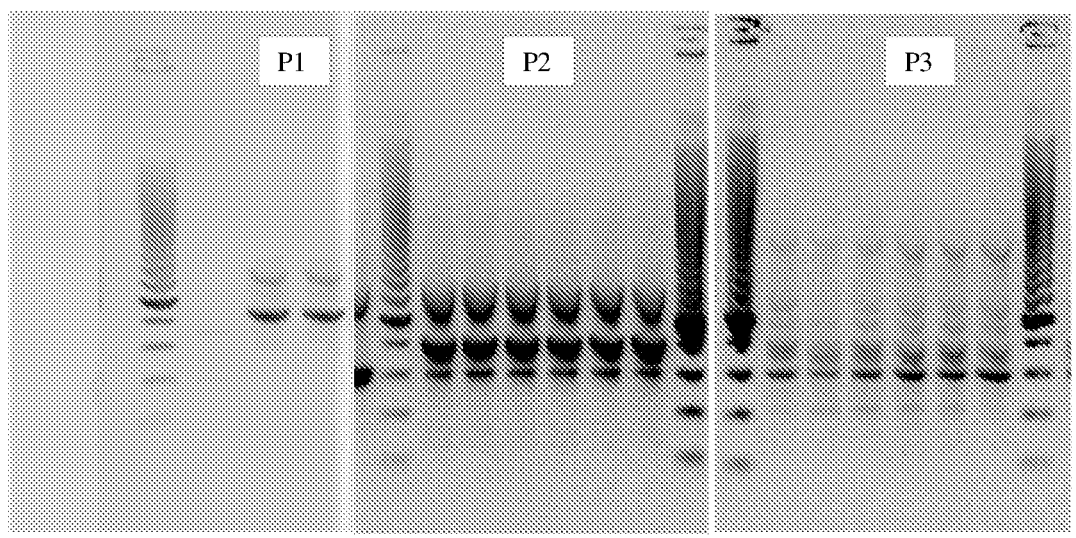
FIG. 8 shows a photograph of a gel displaying a RAPD PCR profile (Primer 1 to 3) for *Bacillus* strain 102. For Primer 1, an intense band appears at 900 base pairs and faint bands appear at 1200 and 1400 base pairs. For Primer 2, intense bands appear at 600, 700, and 1000 base pairs. For Primer 3, an intense band appears at 600 base pairs, double band at 700 and 750 base pairs, double band at 900 and 1100 base pairs, and faint bands appear at 400 and greater than 1800 base pairs.
Figure 9:
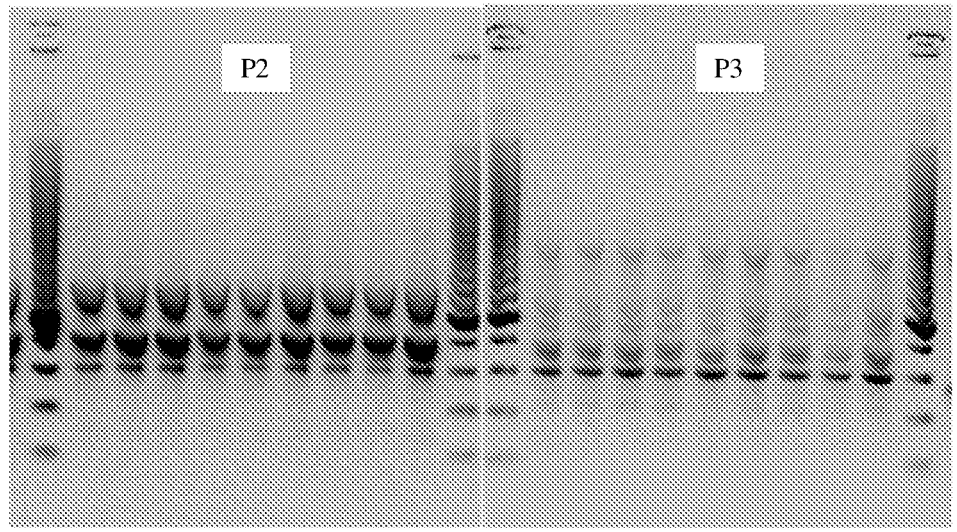
FIG. 9 shows a photograph of a gel displaying a RAPD PCR profile (Primer 2 and 3) for *Bacillus* strain 177. For Primer 2, intense bands appear at 600, 700, and 1000 base pairs. For Primer 3, intense bands appear at 600 base pairs, double band at 700 and 750 base pairs, double band at 900 and 1100 base pairs, and faint bands appear at 400 and greater than 1800 base pairs.
Figure 10:
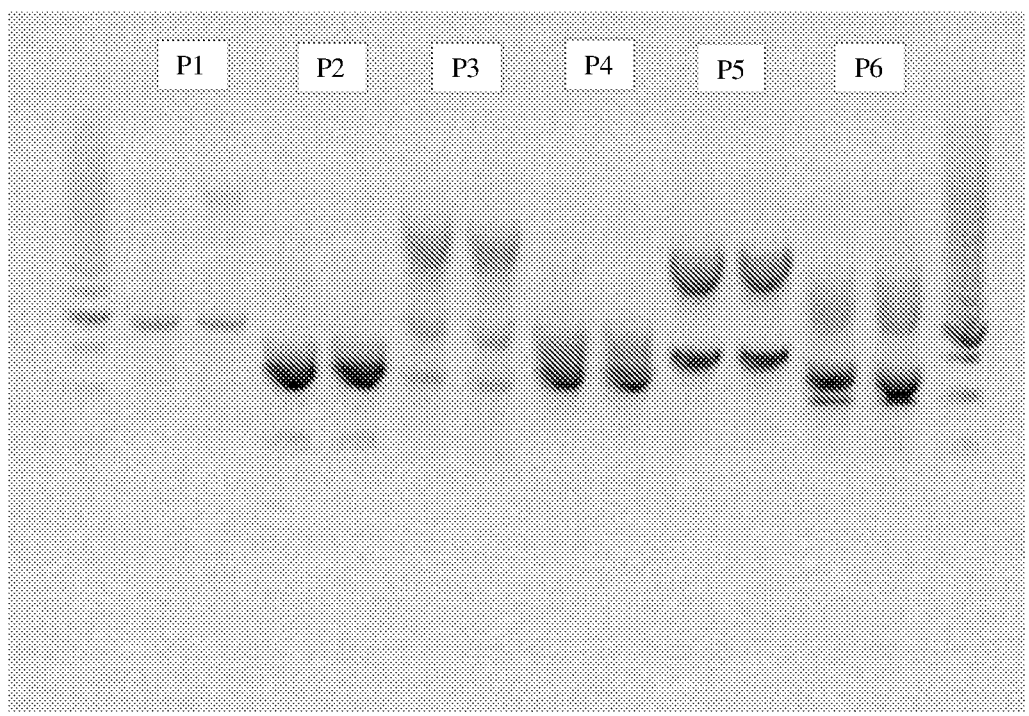
FIG. 10 shows a photograph of a gel displaying a RAPD PCR profile (Primer 1 to 6) for *Bacillus* strain 235. For Primer 1, faint bands appear at approximately 1000 and greater than 1600 base pairs. For Primer 2, an intense band appears at 650 base pairs and a faint band appears at approximately 400 base pairs. For Primer 3, faint bands appear at approximately 400, 600, 1000, and 1400 base pairs.

RT-PCR and subsequent analysis determined that *Campylobacter*, specifically *C. coli*, correlated with both sick (non-prolapsed) baseline animals and those animals that suffered from rectal prolapse ($p<0.05$) sampled approximately 8 weeks later (see FIGS. 4B-4C). Rotavirus C genes were significantly higher in the sick population prior to the prolapse event (see FIG. 4A). It should be noted that *E. coli* virulence factor genes not previously detected during the baseline sampling did appear during the prolapse event, though no significant correlation of these genes to affected animals was apparent.

Several *Bacillus* strains had consistent growth inhibition activity against the majority of *Campylobacter* strains (see FIG. 5).

Based on statistical correlation, *Campylobacter* 16S and *C. coli* genes correlated significantly with nursery animals suffering from rectal prolapse. It was also evident that this microorganism was detected in higher quantities in sick baseline animals eight weeks earlier. Eight *Bacillus* strains, 86, 101, 235, 300, A12, 54, 681, and 721 had strong growth inhibition activity against *Campylobacter* species in an agar plate assay. Thus, strains 86, 101, 235, 300, A12, 54, 681, and 721, may assist in the prevention of prolapse through direct means against *Campylobacter*.

What is claimed is:

1. A method of feeding an animal, the method comprising the step of administering to the animal a feed composition or drinking water comprising an effective amount of an additive comprising an isolated *Bacillus subtilis* strain selected from the group consisting of strains A12 (NRRL No. B-67516), 54 (NRRL No. B-67517), 681 (NRRL No. B-67515), 721 (NRRL No. B-67514), and combinations thereof, wherein the *Bacillus subtilis* strain reduces prolapse in the animal, optionally wherein said additive further comprises one or more *Bacillus* strains selected from *Bacillus subtilis* strain 300 (NRRL No. B-50943), *Bacillus subtilis* strain 101 (NRRL No. B-67218), *Bacillus subtilis* strain 235 (NRRL No. B-67219), *Bacillus subtilis* strain 86 (NRRL No. B-50944), *Bacillus pumilus* strain 102 (NRRL No. B-67276), and *Bacillus pumilus* strain 177 (NRRL No. B-67275).

2. The method of claim 1 wherein the prolapse is selected from the group consisting of vaginal prolapse, uterine prolapse, rectal prolapse, and anal prolapse.

3. The method of claim 2 wherein the prolapse is selected from the group consisting of vaginal prolapse and uterine prolapse.

4. The method of claim 1 wherein the animal is selected from the group consisting of a poultry species, a porcine species, a caprine species, a bovine species, an ovine species, an equine species, and a companion animal.

5. The method of claim 4 wherein the animal is a porcine species and the porcine species is selected from the group consisting of a grow finish pig, a nursery pig, a sow, and a breeding stock pig.

6. The method of claim 1 wherein the *Bacillus subtilis* strain produces an enzyme selected from the group consisting of an α-galactosidase, a protease, a lipase, an amylase, a xylanase, a cellulase, and combinations thereof.

7. The method of claim 1 further comprising the step of administering to the animal another bacterial strain selected from the group consisting of another *Bacillus* strain, a lactic acid bacterial strain, and combinations thereof.

8. The method of claim 1 wherein the *Bacillus subtilis* strain is administered in the feed composition or drinking water at a dose of about $1.0 \times 10^3$ CFU/gram of the feed composition to about $5.0 \times 10^{12}$ CFU/gram of the feed composition.

9. The method of claim 1 wherein the *Bacillus subtilis* strain is administered in the feed composition or drinking water at a dose of about $1.0 \times 10^3$ CFU/gram of the feed composition to about $1.0 \times 10^7$ CFU/gram of the feed composition.

10. The method of claim 1 further comprising the step of administering an antibiotic to the animal.

11. The method of claim 1 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

12. The method of claim 11 wherein the enzyme is an NSPase or a phytase.

13. The method of claim 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

14. The method of claim 1 wherein the additive comprises the *Bacillus subtilis* strain A12 (NRRL No. B-67516).

15. The method of claim 1 wherein the additive comprises the *Bacillus subtilis* strain 54 (NRRL No. B-67517).

16. The method of claim 1 wherein the additive comprises the *Bacillus subtilis* strain 681 (NRRL No. B-67515).

17. The method of claim 1 wherein the additive comprises the *Bacillus subtilis* strain 721 (NRRL No. B-67514).

* * * * *